United States Patent
Zellmer et al.

(10) Patent No.: US 11,844,706 B2
(45) Date of Patent: Dec. 19, 2023

(54) SYSTEM AND METHOD FOR POSITIONING AND ORIENTING AN ORTHOPEDIC IMPLANT

(71) Applicant: Intelligent Implants Limited, Cork (IE)

(72) Inventors: Erik Robert Zellmer, Gothenburg (SE); Rory Kenneth John Murphy, Phoenix, AZ (US); John Michael Zellmer, Gothenburg (SE)

(73) Assignee: Grabango Co., Berkeley, CA (US)

( * ) Notice: Subject to any disclaimer, the term of this patent is extended or adjusted under 35 U.S.C. 154(b) by 703 days.

(21) Appl. No.: 16/825,937

(22) Filed: Mar. 20, 2020

(65) Prior Publication Data

US 2020/0297513 A1 Sep. 24, 2020

Related U.S. Application Data

(60) Provisional application No. 62/821,315, filed on Mar. 20, 2019.

(51) Int. Cl.
*A61F 2/46* (2006.01)
*A61B 34/00* (2016.01)

(52) U.S. Cl.
CPC ............ *A61F 2/4657* (2013.01); *A61B 34/25* (2016.02); *A61F 2/4611* (2013.01);
(Continued)

(58) Field of Classification Search
CPC ..... A61F 2/4455; A61F 2/4657; A61F 2/4684
See application file for complete search history.

(56) References Cited

U.S. PATENT DOCUMENTS 3,842,841 A 10/1974 Brighton et al.
4,175,565 A 11/1979 Chiarenza et al.
(Continued)

FOREIGN PATENT DOCUMENTS

EP 3789079 A1 3/2021
WO 2013188380 A1 12/2013
WO 2014089299 A3 10/2014

OTHER PUBLICATIONS

Laughner JI, et al. (2013) A Fully Implantable Pacemaker for the Mouse: From Battery to Wireless Power. PLOS ONE 8(10): e76291. https://doi.org/10.1371/journal.pone.0076291, Oct. 23, 2013.
(Continued)

*Primary Examiner* — Andrew Yang
(74) *Attorney, Agent, or Firm* — Alpine Patents LLC; Brian Van Osdol

(57) ABSTRACT

A system and method for positioning and orienting an orthopedic implant that includes an implant body; a sensor system integrated into the implant body, the sensor system comprising of at least a plurality of electrodes positioned within the implant body such there is at least one exposed region on the surface of the implant body for each electrode of the plurality of electrodes; a sensor processing control system communicatively coupled to the sensor system, the sensor processing control system configured with instructions that when executed cause the sensor processing control system to collect sensor data from the sensor system and generate adjacency data from the sensor data; and an implant feedback system, that updates state based in part on the adjacency data.

19 Claims, 18 Drawing Sheets

(52) U.S. Cl.
CPC ...... *A61F 2/4684* (2013.01); *A61B 2034/254* (2016.02); *A61F 2002/4633* (2013.01); *A61F 2002/4666* (2013.01)

(56) References Cited

U.S. PATENT DOCUMENTS

| | | | |
|---|---|---|---|
| 4,313,438 | A | 2/1982 | Greatbatch |
| 4,690,144 | A | 9/1987 | Rise et al. |
| 4,690,166 | A | 9/1987 | Howeth |
| 5,056,518 | A | 10/1991 | Pethica et al. |
| 5,330,477 | A | 7/1994 | Crook |
| 5,358,514 | A | 10/1994 | Schulman et al. |
| 5,441,527 | A | 8/1995 | Erickson et al. |
| 5,458,627 | A | 10/1995 | Baranowski, Jr. et al. |
| 5,565,005 | A | 10/1996 | Erickson et al. |
| 5,974,342 | A | 10/1999 | Petrofsky |
| 5,989,289 | A | 11/1999 | Coates et al. |
| 6,120,502 | A | 9/2000 | Michelson |
| 6,292,699 | B1 | 9/2001 | Simon et al. |
| 6,400,990 | B1 | 6/2002 | Silvian |
| 6,582,467 | B1 | 6/2003 | Teitelbaum et al. |
| 6,605,089 | B1 | 8/2003 | Michelson |
| 7,104,986 | B2 | 9/2006 | Hovda et al. |
| 7,309,338 | B2 | 12/2007 | Cragg |
| 7,324,852 | B2 | 1/2008 | Barolat et al. |
| 7,359,755 | B2 | 4/2008 | Jones et al. |
| 7,455,672 | B2 | 11/2008 | Michelson |
| 7,578,819 | B2 | 8/2009 | Bleich et al. |
| 7,935,116 | B2 | 5/2011 | Michelson |
| 8,014,873 | B2 | 9/2011 | Jones et al. |
| 8,078,282 | B2 | 12/2011 | Nycz |
| 8,078,283 | B2 | 12/2011 | Cowan et al. |
| 8,206,387 | B2 | 6/2012 | Michelson |
| 8,463,401 | B2 | 6/2013 | Jones et al. |
| 8,666,471 | B2 | 3/2014 | Rogers et al. |
| 8,718,777 | B2 | 5/2014 | Lowry et al. |
| 8,740,879 | B2 | 6/2014 | Martinson et al. |
| 8,771,360 | B2 | 7/2014 | Jimenez et al. |
| 8,838,249 | B2 | 9/2014 | Nycz |
| 8,903,502 | B2 | 12/2014 | Perryman et al. |
| 10,292,831 | B2 | 5/2019 | Zellmer et al. |
| 10,617,880 | B2 | 4/2020 | Zellmer et al. |
| 11,097,096 | B2 | 8/2021 | Linden et al. |
| 2003/0078634 | A1 | 4/2003 | Schulman et al. |
| 2004/0249373 | A1 | 12/2004 | Gronemeyer et al. |
| 2005/0033393 | A1 | 2/2005 | Daglow |
| 2005/0216702 | A1 | 9/2005 | Paolucci et al. |
| 2007/0250045 | A1 | 10/2007 | Trieu |
| 2008/0039901 | A1 | 2/2008 | Kronberg et al. |
| 2008/0294211 | A1 | 11/2008 | Moffitt |
| 2008/0300660 | A1 | 12/2008 | John |
| 2009/0062886 | A1 | 3/2009 | O'Handley et al. |
| 2010/0168829 | A1 | 7/2010 | Schwartz et al. |
| 2010/0204551 | A1 | 8/2010 | Roche |
| 2010/0292756 | A1 | 11/2010 | Schneider |
| 2011/0009728 | A1 | 1/2011 | Schouenborg |
| 2011/0087315 | A1 | 4/2011 | Richardson-Burns et al. |
| 2011/0092948 | A1 | 4/2011 | Shachar et al. |
| 2011/0301716 | A1 | 12/2011 | Sirivisoot et al. |
| 2013/0150970 | A1 | 6/2013 | Thaiyananthan |
| 2013/0165991 | A1 | 6/2013 | Kim et al. |
| 2013/0296940 | A1 | 11/2013 | Northcutt et al. |
| 2014/0114382 | A1 | 4/2014 | Kim |
| 2014/0133123 | A1 | 5/2014 | Prasannakumar et al. |
| 2014/0275847 | A1 | 9/2014 | Perryman et al. |
| 2014/0277260 | A1 | 9/2014 | Khalil et al. |
| 2014/0371823 | A1 | 12/2014 | Mashiach et al. |
| 2015/0018728 | A1 | 1/2015 | Gross et al. |
| 2015/0134061 | A1 | 5/2015 | Friis et al. |
| 2015/0187320 | A1 | 7/2015 | Ren |
| 2016/0270927 | A1* | 9/2016 | Zellmer .................. A61F 2/28 |
| 2017/0007420 | A1 | 1/2017 | Stevenson et al. |
| 2017/0246448 | A1 | 8/2017 | Lenoble et al. |
| 2018/0078774 | A1 | 3/2018 | Strommer et al. |
| 2018/0208992 | A1 | 7/2018 | Langevin et al. |
| 2018/0310964 | A1 | 11/2018 | Stevenson et al. |
| 2019/0224022 | A1 | 7/2019 | Zellmer et al. |
| 2019/0247198 | A1 | 8/2019 | Zellmer et al. |
| 2020/0107940 | A1 | 4/2020 | Murphy et al. |
| 2020/0108252 | A1 | 4/2020 | Zellmer et al. |
| 2020/0206516 | A1 | 7/2020 | Zellmer et al. |
| 2020/0352723 | A1 | 11/2020 | Jimenez et al. |

OTHER PUBLICATIONS

WIPO European Searching Authority, "PCT2016000482 WO Search And Opinion", dated Jul. 7, 2016.

* cited by examiner

Providing an implant body with a sensor system for surgical placement in a defined body cavity S110

Collecting sensor data from the sensor system and converting the sensor data to tissue adjacency data S120

Determining implant adjacencies S122

Determining implant orientation S124

Reporting the tissue adjacency data through a feedback interface S130

FIGURE 8

Implant Trial Setting Target Orientation

Medical Impant Comparing to Target

Implant Trial Setting Target Tissue Alignment

Medical Impant Comparing to Target

SYSTEM AND METHOD FOR POSITIONING AND ORIENTING AN ORTHOPEDIC IMPLANT

CROSS-REFERENCE TO RELATED APPLICATIONS

This Application claims the benefit of U.S. Provisional Application No. 62/821,315, filed on 20 Mar. 2019, which is incorporated in its entirety by this reference.

TECHNICAL FIELD

This invention relates generally to the field of implant surgery, and more specifically to a new and useful system and method for positioning and orienting an orthopedic implant.

BACKGROUND

Spinal fusion is one of the most commonly performed surgical procedures within the US and in Europe. The goal of spinal fusion surgery is to introduce bone growth between two or more vertebrae, fusing them into a single, continuous unit. Spinal fusion surgery is performed in the lumbar, cervical and thoracic regions, and fusions within each region are associated with a different set of complications. Even so, most complications following spinal fusion can be generalized into two broad categories: non-fusions, where the vertebrae are not fused into a singular unit due to insufficient bone formation within the fusion space; heterotopic ossification, where bone growth damages or impinges on tissue causing harm or discomfort to the patient. Examples of heterotopic ossification includes: Anterior osteophyte formation causing mass effect on the esophagus leading difficulty of swallowing (cervical fusions); ossification of the posterior longitudinal ligament; and formation of posterior osteophyte and/or other excessive posterior bone growth pressuring the spinal cord and/or spinal nerves.

Many contemporary spinal fusion hardware and biologics include designs to address the problems associated with non-unions, with little regard to heterotopic ossification. For example, commonly used biologics, particularly recombinant human bone morphogenetic protein (rhBMP-2), have been used to reduce non-fusion rates by increasing bone formation in the fusion space and the volume surrounding it. While clinically proven to decrease non-unions, numerous studies have shown that the biologic causes a host of side effects including but not limited to cancer, tissue swelling, growth of benign tissue, teratogenicity, pathological heterotopic ossification, nerve injury and spinal cord injury. While not all side effects caused by rhBMP-2 are related to heterotopic ossification, many are. As such, the biologic represents an illustrating example of how, nonspecific, unguided osteoinduction can be harmful to a patient and the delicate balance between increasing fusion rates and avoiding heterotopic ossification.

A second method utilized in reducing non-union rates is electrical stimulation. When mechanical stress is exerted on bone, an electric field is created. In the body, this electrical field constitutes a signal causing a physiological response resulting in osteoinduction or osteolysis. Consequently, it is possible to cause osteoinduction or osteolysis by introducing an electrical field in the volume within and surrounding a segment of bone. In volumes where the current density is above a certain threshold, osteoinduction is achieved if the polarity of the field in the region is electronegative while bone in regions where the field is electropositive undergoes osteolysis.

Currently, some risk of non-unions may be reduced using implantable or external electrical stimulators. Many existing implantable stimulators use hermetically-sealed, constant-current DC power sources attached to one or more electrodes, which can be large, unwieldy and prone to infection or complications. In addition, the electrodes of these implantable systems are long and are liable to break. Since implantable systems are designed to be placed along the length of the spine covering multiple vertebrae, they often migrate and may cause injury.

External stimulators are marketed by Biomet, Orthofix International and DJO Global. External stimulation systems use an AC signal generator connected to electrodes placed on the skin or to an induction coil, which introduces electrical fields in the volume of the spine and the volume enveloping it through induction.

The above mentioned systems suffer product-specific disadvantages such as the complicated implantation procedures for the implantable systems and stringent patient compliance requirements for the external stimulators. Additionally, the risk of heterotopic ossification is not addressed by any present system. Specifically, similarly to rhBMP-2, existing electrical stimulation systems are aimed at reducing non-union rates through nonspecific, unguided osteoinduction.

As the technology and usage of spinal fusion hardware improve, a greater emphasis needs to be placed on how to monitor the hardware, how to implant the hardware, and to choose the correct size and shape of the hardware to maximize its effectiveness. Thus, there is a need in the orthopedic medical field to create a new and useful system and method for monitoring the position and orientation of an orthopedic implant and assessing the implantation site. This invention provides such a new and useful system and method.

BRIEF DESCRIPTION OF THE FIGURES

FIG. 8 is a flowchart of a method of preferred embodiment; and

DESCRIPTION OF THE EMBODIMENTS

The following description of the embodiments of the invention is not intended to limit the invention to these embodiments but rather to enable a person skilled in the art to make and use this invention.

1. Overview

Figure 1:
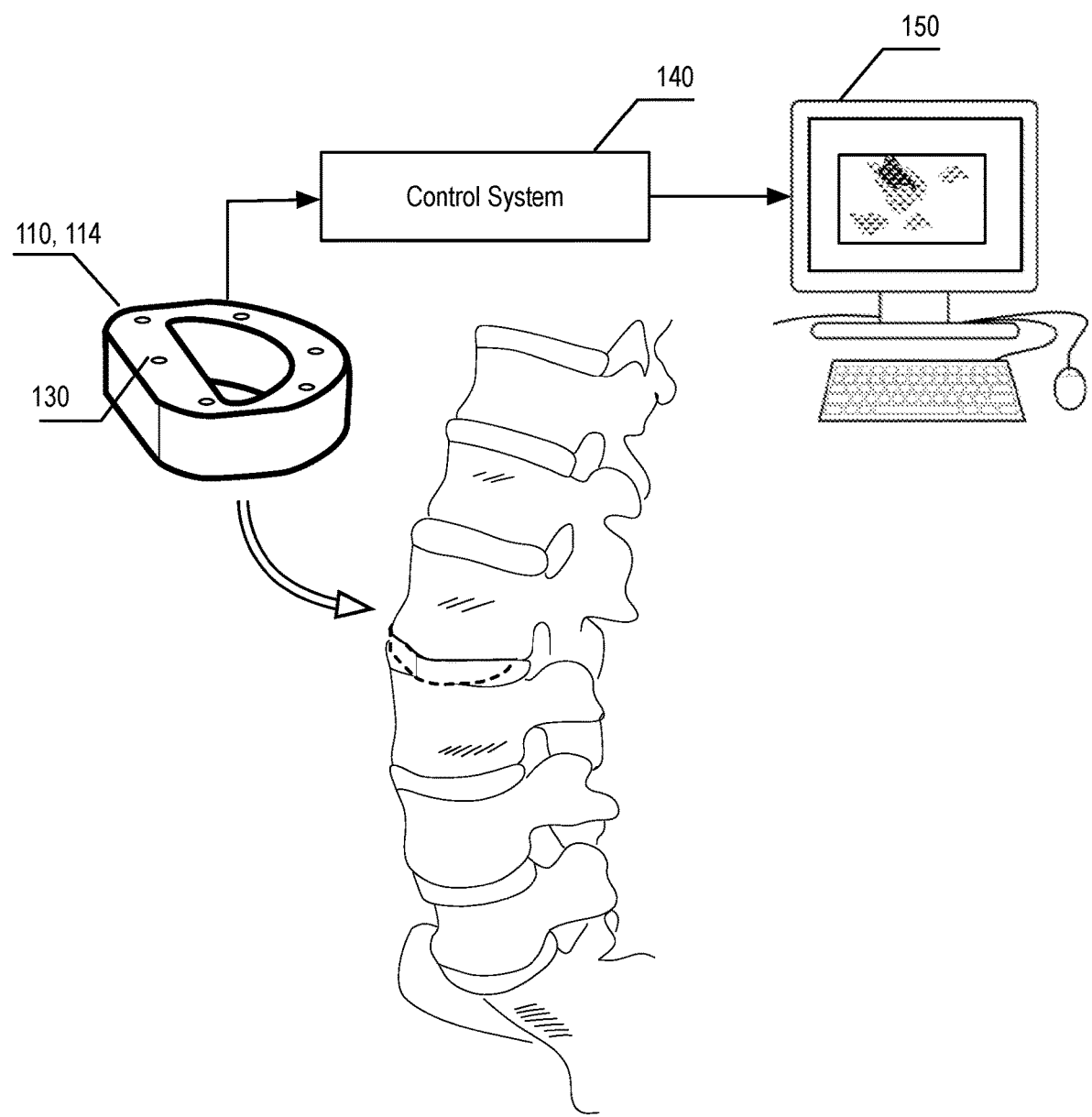
FIG. 1 is a schematic representation of a system of preferred embodiment.

As shown in FIG. 1, a system and method for positioning and orienting an orthopedic implant make use of a sensing system integrated into the surface of an implant body that can be used to report on adjacent tissue information. The system and method may be used as a tool during a surgery procedure for sizing a surgically extracted cavity that will receive a medical implant and/or for assisting in properly positioning an implant. The system and method may additionally or alternatively have use after surgery by enabling reporting on implant position and orientation within the body, which can help detect drift and/or other issues.

The system and method leverages sensing capabilities of one or more sensor subsystems of the sensing system to analyze and track the conditions in proximity of the implant body. These sensor subsystems may use impedance measurement to classify tissue, use pressure sensors to track cavity size, use various orientation tracking techniques for reporting position and orientation, and/or use other sensing systems. The implant body is structurally in the form of a medical implant prosthesis or an approximation of an implant such as a spine cage used in spinal fusion surgery. In one variation, the system and method may be used to enable a sensor enhanced implant trial (sometimes called "trial prosthesis" or simply "trial") that can serve as a surgical tool. As an implant trial, an implant trial body can serve as a structural proxy to an actual medical implant for the purposes of probing and sizing. In another variation, the system and method may be used to enhance sensor enhanced capabilities within a medical implant. For example, the sensing capabilities and reporting may be used during surgical implantation or monitoring of orthopedic implants like a spine cage used for spinal fusion. Some variations, the system and method can use cooperative operation between a sensor-enhanced implant trial and a sensor-enhanced medical implant such as using sensed data from the implant trial to provide feedback on the current status and position of a medical implant during final positioning of a surgery.

In the implant trial variation, the implant trial variation can preferably provide useful feedback to medical professionals concerning the type of tissue in the cavity, the size and shape of the cavity, an appropriate size and shape for a selected medical implant, and/or other information. The implant trial variation of the system and method may assist in predetermining an appropriate position, geometry, and orientation of an implant prior to placing the actual medical implant body in a patient. In an implant trial variation, the implant trial may be connected to a rigid arm attachment. As an example, of the trial variation, a surgeon may initially surgically extract tissue to form an initial cavity where the medical implant will be placed. Then the surgeon can place the sensor-enhanced implant trial into the cavity. Various sensors on the surface of the implant trial can detect the tissue type, pressure, orientation, and/or other data. This data on the adjacent tissue can be provided as feedback to the surgeon so that they may adjust the size of the cavity or select an appropriately sized medical implant. Impedance measurements between electrodes on the surface of the implant body may determine the tissue adjacent to the implant (e.g. bone), thereby determining if the cavity is properly prepared for receiving a medical implant. Additionally, pressure measurements on the implant surface may additionally aid in determining the positioning of the implant and help determine the appropriate size of the implant and/or the cavity.

Figure 9:
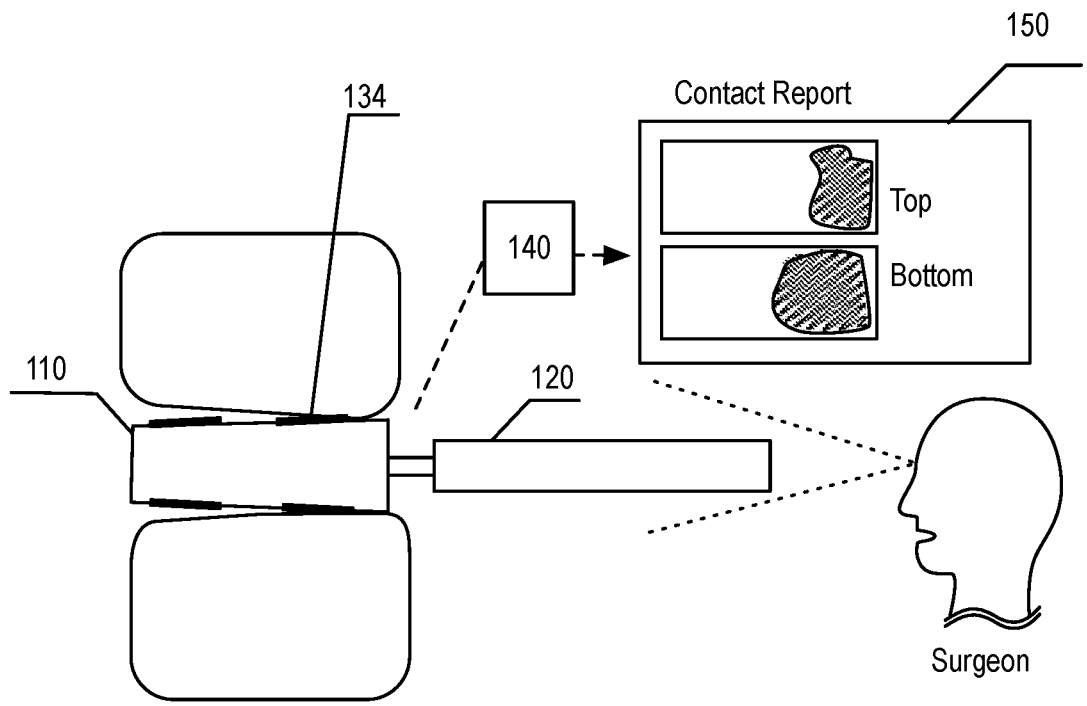
FIGS. 9 and 10 are schematic representations of potential scenarios encountered during surgery that can be reported by a system and method
Figure 10:
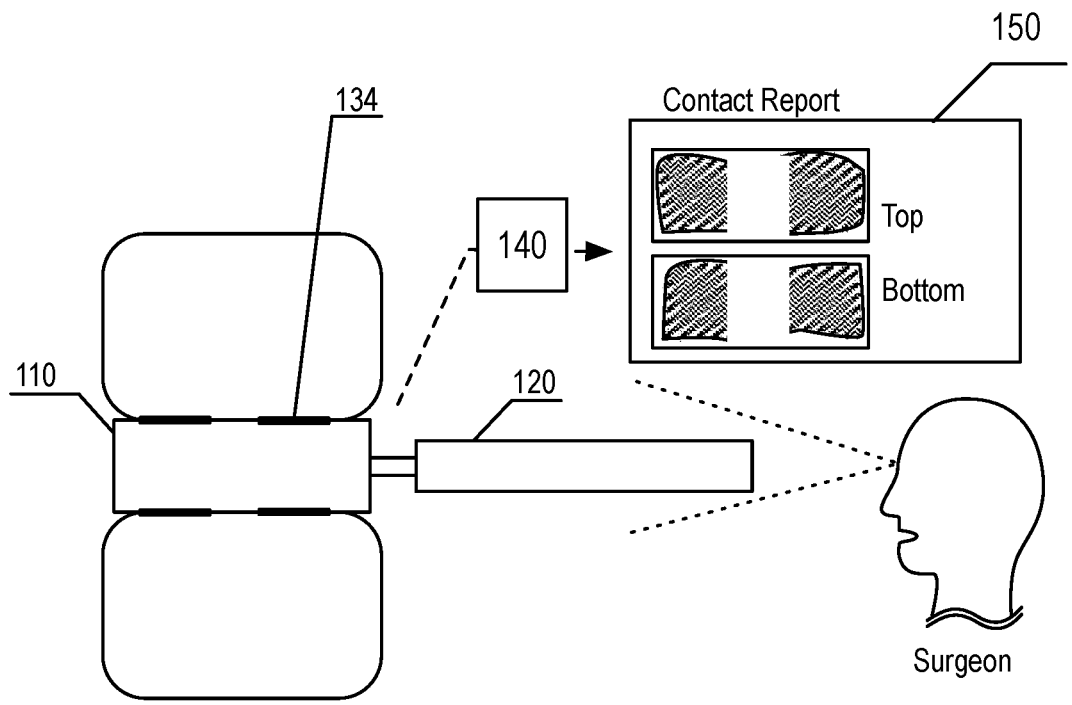

In one exemplary scenario for a spinal fusion surgery, a surgeon may initially perform a partial or full discectomy, removing the disc between two vertebrae. Then the surgeon may file on the endplates of the vertebrae to start bleeding, which may recruit osteoblasts to the site. It is into this extracted cavity that a surgeon will attempt to insert the implant (an intervertebral fusion device, also called "spine cage" or simply "cage") in a position where bone contact is established along the surfaces of the cage. However, the surgeon may only visually inspect the bone contact on the outer edges of site. In some cases, the profiles of the insertion site, adjacent bone, and/or the cage may not align fully across the entirety of the surface as shown in FIG. 9. This may be used to select a different size/type trial with a better fit as shown in FIG. 10 and thereby select a different medical implant. Additionally, the state of the extracted cavity can have a significant impact on the success of the surgery. If too much of the end plate is shaved off then there is a risk the implant could subside into the bone over time. If disc material is still present, desired bone growth won't be able to grow through the disc material. The system and method may address such issues by providing a technical solution by which the extracted cavity can be inspected. For example, an impedance system of an implant can report the level of contact and possibly the regions of contact. This reporting may be used with a trial cage to assess the right size of a cage or with the actual cage implant. As another example, the system and method may also determine if too little or too much bone has been cleaned/filed away since the outermost, and hardest, layer of bone (cortical bone) that is cleaned/filed away first has a different impedance than the, softer, trabecular bone underneath. Excessive cleaning/filing can weaken the endplate. Similarly, the impedance of the tissue in the cavity may reveal the presence of unwanted disk at or adjacent to the intended site of actual medical implant insertion. As shown in FIG. 9, the system and method can report when the cage is aligned and compatible with the defined implant cavity such that appropriate bone/tissue alignment is achieved.

As the goal of spinal fusion surgery is to fuse adjacent vertebrae, a potential major benefit of the system and method is to increase the likelihood of spinal fusion. Improved positioning of the spinal implant may help increase the implant surface area near or in contact with bone and minimize the distance and amount of bone growth required for spinal fusion.

As a related variation, the sensor-enhanced implant trial variation of the system and method may additionally or alternatively be used to supply the collected data to another digital system, which can use this data in a variety of ways. In some variations, the data may be used to inform a surgical robot of the conditions in the cavity. For example a multi-dimensional map of tissue surrounding the cavity may show which sub-regions of the cavity could benefit from additional tissue extraction and which sub-regions of the cavity have sufficiently been extracted. The surgical robot could use this data to determine a control plan for subsequent tissue extraction. In another variation, the collected data can be supplied to another body imaging device such that collected data can be synchronized to additional imaging data. For example, highlighting tissue map data on a CT scan.

In a variation applied to a functioning medical implant, the system and method can use the position and orientation monitoring capabilities of the system and method to report on the status of the medical implant within a patient's body. This functionality could be used during surgery or post surgery. During surgery, the system and method may enable a more precise desired positioning of the implant. For example, a surgeon could have a generated map of the tissue adjacent to the implant during the surgery to confirm it was properly placed. After surgery, the system and method may allow monitoring of a medical implant to determine the implant's position and orientation, helping to make sure it is still in the proper place. In one preferred application, the implant is an orthopedic implant. For example, one preferred use case is for a spinal fusion implant (e.g., a spine cage). Impedance measurements between electrodes on the surface of the implant body may determine the tissue adjacent to the implant (e.g. bone), thereby also determining the relative position of the implant body with respect to the vertebrae of the patient. Additionally, pressure measurements may further show the status of the implant with respect to adjacent bone tissue. The orienting system may function as a directional antenna array giving the orientation of the implant with respect to the non-implant orienting component.

The system and method may provide a number of potential benefits. The system and method are not limited to always providing such benefits, and are presented only as exemplary representations for how the system and method may be put to use. The list of benefits is not intended to be exhaustive and other benefits may additionally or alternatively exist.

One potential benefit of the system and method is enhanced visibility into the surgical site that can assist a surgeon and other medical professionals when performing an implant surgery. As discussed above, the system and method can provide insights that can be used to adjust preparation of a site, and/or for selecting the appropriate medical implant. Another potential benefit of the system and method is easier and better positioning of a medical implant. The arm attachment may better facilitate manipulation of the implant enabling faster and more precise placement of the implant. The enhanced sensing of a medical implant as enabled through the system and method can remove the guesswork when placing an implant into position during surgery.

As another potential benefit of the system and method is a new sensing modality that can be used by other medical systems. For example, robotic surgical systems or other tools may use the data generated by the system and method.

Another potential benefit of the system and method is a quicker assessment of implant failure. The ability to monitor vertebrae adjacency and orientation of the implant may allow for immediate determination that the implant has moved out of position or is in the wrong orientation with respect to the vertebrae. This quick assessment may further lead to be better patient care, intervention, and recovery.

One potential benefit of the system and method is improved analytics leading to potential future benefits from research. More precise data of the positioning of the implant both during and after surgery may allow for the detection of positioning trends that lead to the design of better implants and better patient care.

Another potential benefit due to improved analytics is that this may also reduce the reliance of X-ray and CT scans (computed tomography scans) to determine the position and/or status of an implant thereby reducing patient exposure to ionizing radiation. Traditionally, X-ray, CT scans, and other imaging techniques were needed to visualize and monitor position and orientation of an implant within a body. The system and method can enable unique technical abilities to report on position and orientation to not only replace such costly and risk imaging techniques, but also to provide a technique whereby the status of the implant can be more regularly checked.

The system and method are primarily described as applied to spinal fusion orthopedic implants, but the system and method may be implemented with any series of orthopedic implants, implant trials, or other types of implant bodies. The system and method may additionally be implemented with any general type of implant wherein tissue adjacency and/or implant orientation may be a factor.

2. System

As shown in FIG. 1, a system for positioning and orienting an orthopedic implant of a preferred embodiment includes: an implant body 110; a sensor system 130 with a plurality of sensors distributed across the surface of the implant body; a sensor processing control system 140 configured to process sensor data from the sensor system; and an implant feedback system 150.

Figure 2:
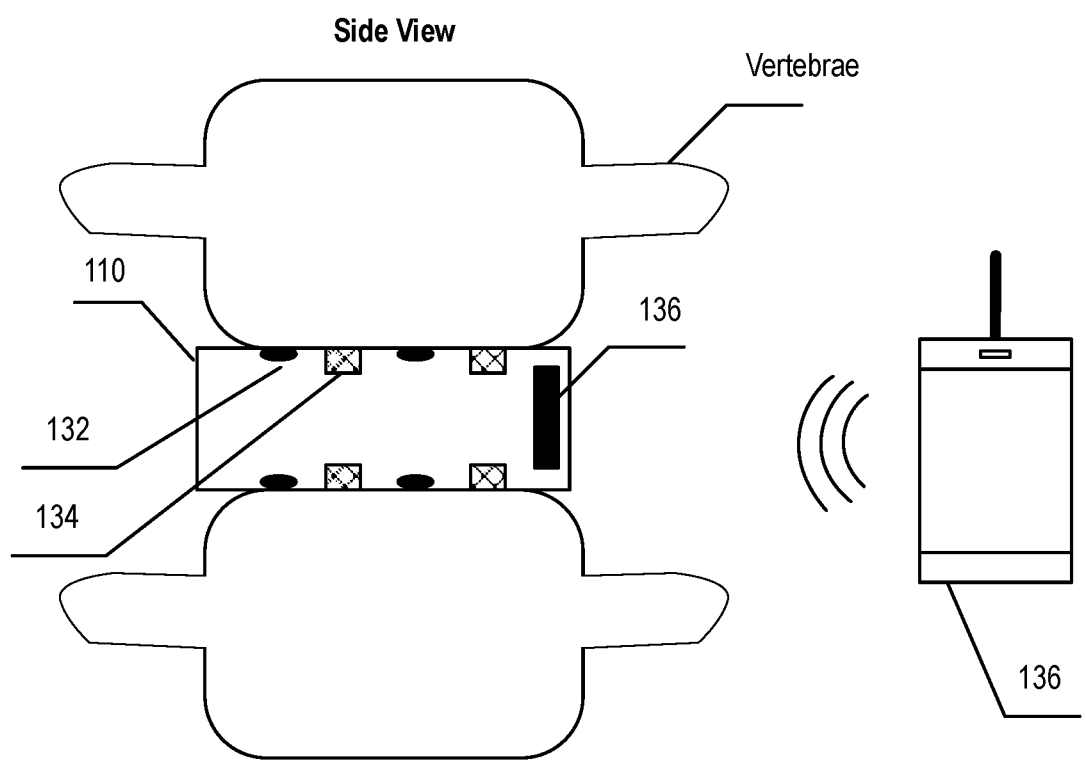
FIG. 2 is a detailed schematic representation of a side view of a system variation with multiple sensor sub-systems.

In some variations, the sensor system 130 may include one or more types of sensor subsystems, which could include an array of electrodes for impedance measurements 132, a pressure sensor system 134, an orienting system 136, and/or other sensor sub-systems as shown in FIG. 2. The sensor processing control system may be part of a larger digital or electronically implemented control system that modifies the functionality of certain electronic components. The system may further comprise any additional components such as a power system that provides power to the components.

The system functions to determine and monitor the tissue in adjacent proximity to the implant body. The system may additionally or alternatively provide position and orientation information of the implant body no, which may be used for better positioning of the implant body.

Figure 3:
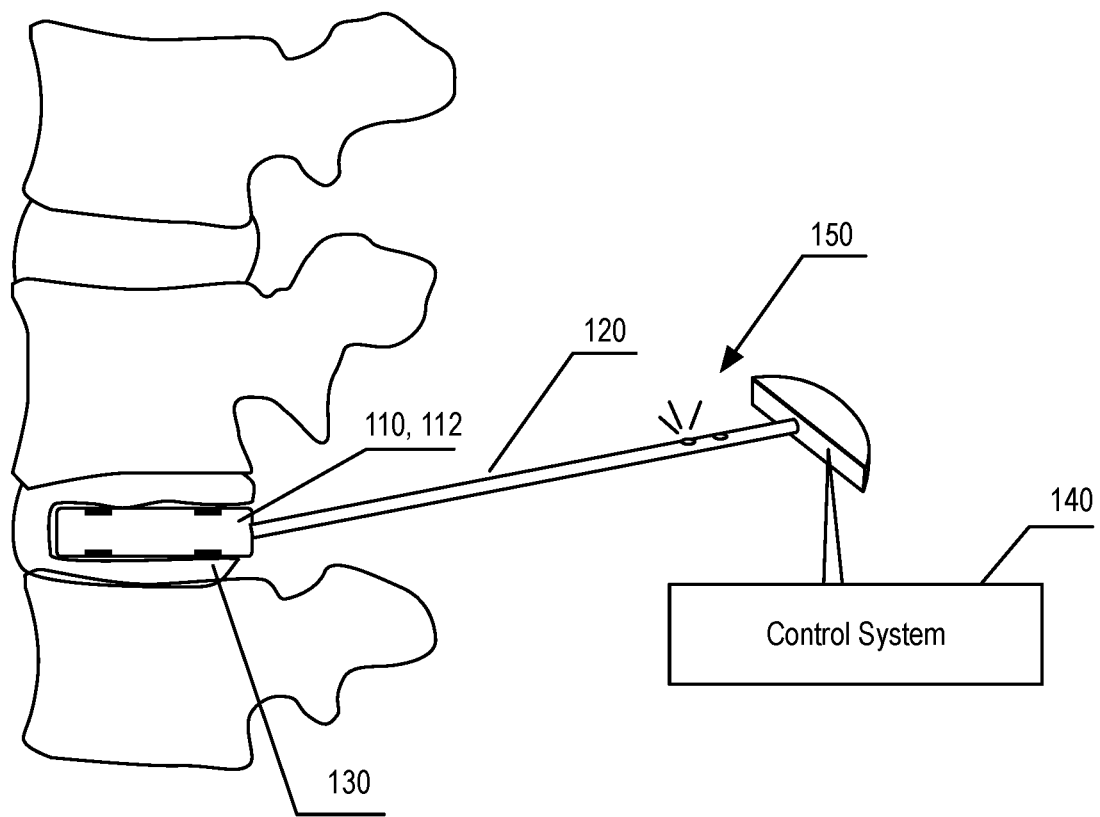
FIG. 3 is an alternative schematic representation of a system of preferred embodiment for an implant trial.

As shown in FIG. 3, the system may additionally include an arm attachment 120 or other mechanism that may serve as a physical appendage to aid in positioning during surgery. The system is preferably implemented with an orthopedic implant body type (either as a trial unit or an actual functional medical implant), but may more generally be implemented with any type of implant.

In one particular variation, the system includes an implant body 110 made of a solid rigid structure; a sensor system 130 integrated into the implant body; a sensor processing control system 140 communicatively coupled to the sensor system 130, the sensor processing control system 140 configured with instructions that when executed cause the sensor processing control system 140 to collect sensor data from the sensor system 130 and generate adjacency data from the sensor data; and an implant feedback system 150 that updates state based in part on the adjacency data.

In one variation, the sensor system can include a plurality of electrodes 132 positioned within the implant body such that there is at least one exposed region on the surface of the implant body for each electrode of the plurality of electrodes 132

In such an electrode variation, the sensor processing control system 140 can include a configuration to measure impedance across multiple pairs of electrodes from the plurality of electrodes 132; and wherein instructions to generate adjacency data from the sensor data generate a map of tissue classifications from the measured impedance. Impedance measurements are preferably obtained for multiple sub-regions adjacent to the implant body 110, which can be used in classifying tissue type or other tissue related information. In one particular implementation (e.g., such as for a spine cage) the plurality of electrodes 132 can include a subset of electrodes that is positioned on a first external face of the implant body and a second subset of electrodes that is positioned on a second external face of the implant body. The first and second external faces can be on opposite sides of the implant body (e.g., top and bottom). In this implementation variation, the map of tissue classifications can be mapped for the first and second external faces.

In some variations, an electrode-based sensor system can be used in combination with pressure sensors. In such an impedance and pressure sensing variation, the sensor system 130 of the electrode variation described above may additionally include a plurality of pressure sensors; and wherein the instructions to generate adjacency data from the sensor data generate a sizing/topography map of adjacent tissue based in part on pressure data collected from the pressure sensors and the map of tissue classifications.

Figure 16:
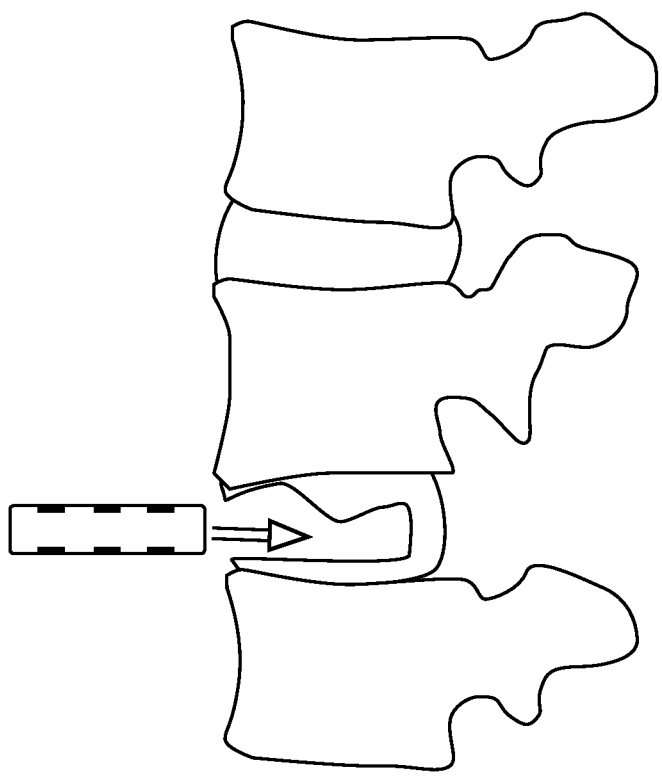
FIG. 16 is a schematic representation of generation of a sizing map corresponding to an extracted cavity during surgery.
Figure 16:
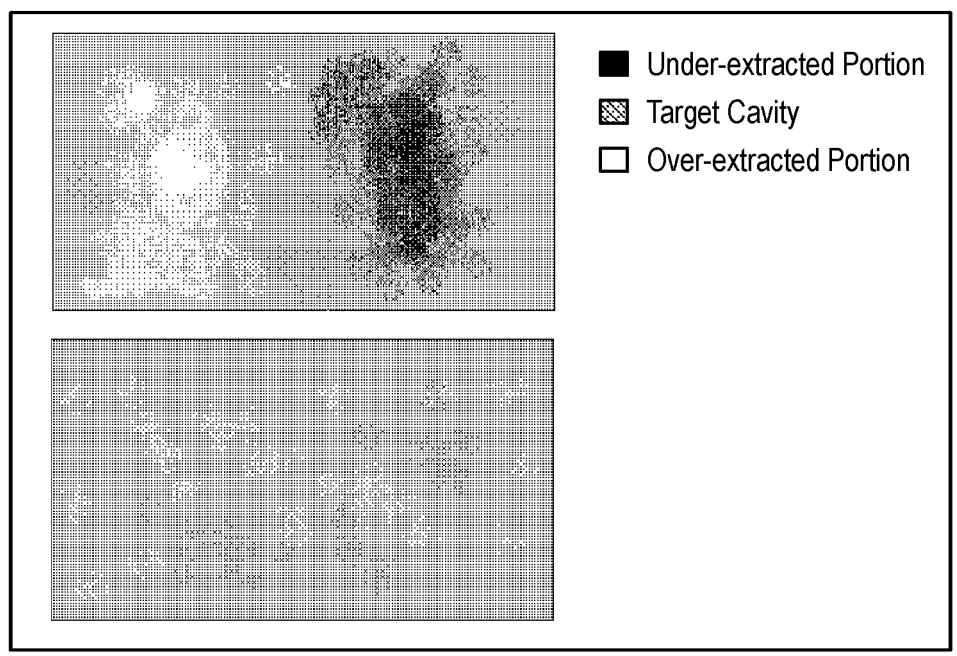

In other variations, the system may include a pressure system used separately or independently from an electrode system. In a pressure sensing variation, the sensor system 130 can include a plurality of pressure sensors; and the instructions of the sensor processing control system 140 to generate adjacency data from the sensor data generate a sizing map based in part on pressure data collected from the pressure sensors. The pressure sensors generate or otherwise collect pressure data from the pressure sensors. The pressure sensors are preferably distributed across the surface of the implant body no. In one variation, the plurality of pressure sensors includes a subset of pressure sensors that is positioned on a first external face of the implant body 110 and a second subset of electrodes that is positioned on a second external face of the implant body no. The first and second external faces can be on opposite sides of the implant body 110 (e.g., top and bottom). In such a variation, the sizing map can include sizing data mapped for the first and second external faces. The sizing map can be used in generating a graphical representation of the extracted cavity. When used with a sensor-enhanced implant trial, the pressure on an implant trial shows the sub-regions of an extracted tissue that are under-extracted and/or over-extracted as shown in FIG. 16. It can be a useful tool that can provide feedback (e.g., through the feedback system 150) so that a surgeon can better size an extracted site and/or place/size an implant.

In other variations, the system can include an orienting system 136. The orienting system 136 is preferably configured to report the orientation of the implant body corresponding to the adjacency data. However, the orientation data may be used independent of adjacency data. In an orienting variation, the sensor system 130 includes an orienting system. This may be an inertial measuring unit, accelerometer, gyroscope, or other type of orientation sensing system. Orientation data may be communicated to an external system. In one variation, the sensor system 130 includes an orienting system 136 that includes an oriented antenna integrated into the implant body 110 and an external antenna array that is used to interrogate and determine the orientation of the oriented antenna. The external antenna array can include multiple antennas with multiple orientations. The sensor processing control mode can include an orienting function mode with instructions configured such that detected strength coupling between the oriented antenna and the antenna array is used to determine the relative orientation of the oriented antenna (i.e., determining relative orientation between the implantable antenna and the external antennas).

As discussed above, variations of the system may be applied to different form factors such as a trial variation, a medical implant variation, and a variation where an implant trial and medical implant can both be sensor-enhanced for cooperative operation during a surgery.

In an implant trial variation, the implant body 110 is an implant trial body 112. An implant trial variation will generally include an arm attachment 120 that extends from and physically couples to the implant trial body 112. The arm attachment 120 may removably couple to the implant body through an attachment mechanism. Alternatively, the arm attachment 120 may be substantially fixed to the implant body. The implant trial variation can preferably be used as a tool during surgery to provide adjacency data for the extracted cavity to help a surgeon determine the status of the cavity (e.g., where is the tissue properly extracted and exposed and where is more extraction needed) and selection of an appropriate medical implant. In some trial variations, the arm attachment 120 may house electrical components such as the sensor processing control system, a power system, user feedback elements, and/or any suitable components. In one variation, the arm attachment 120 may be a conduit for conductive connections from the sensor system 130 and either a coupled device or a wireless communication module.

In a medical implant variation, the implant body no can be a medical implant intended for implantation in a body. Herein medical implant is used to refer to an implant variation intended for sustained implantation. One preferred type of implant body 110 is a spinal implant or intervertebral body fusion device, also called a spine cage. Other suitable type of orthopedic implants or other types of implants may additionally be used.

Figure 17:
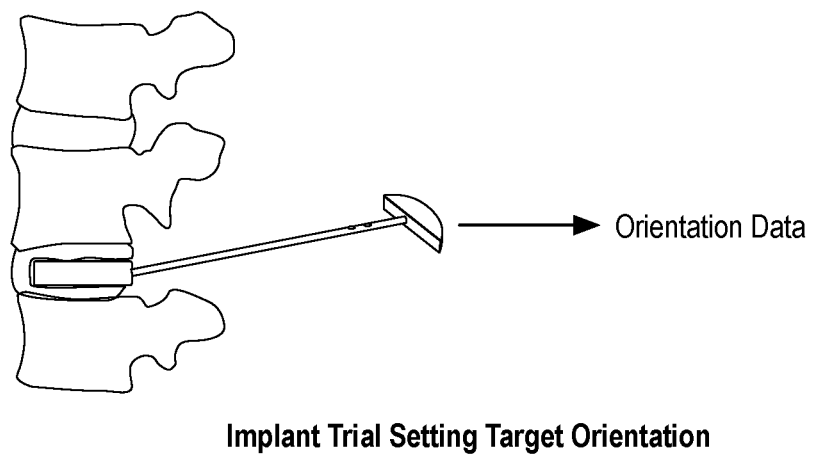
FIGS. 17 and 18 show two exemplary variations of an implant trial system and a medical implant system being used in cooperation.
Figure 17:
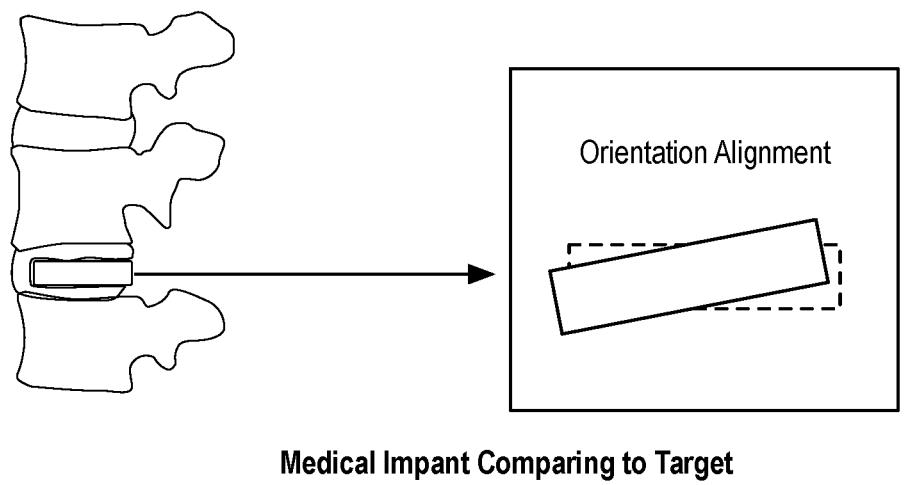

As discussed, some variations may make use of two enhanced implants—one an implant trial and another medical implant. These may be used so that the sensor system 130 can collect an initial adjacency map to aid the surgeon to determine a target orientation and position for the implant. When inserting the medical implant, an orienting system 136 and/or other sensor system 130 can make readings that can be compared to the data collected by the implant trial such that a target orientation and position can be achieved. As shown in FIG. 17, an implant trial system could establish a target orientation, and then user interface feedback could be generated when positioning a medical implant showing the correspondence to the target orientation. Additionally or alternatively, when multiple medical implants are inserted at the same time, relative orientation and positioning may be sensed and guided. In some cases, the sensing capabilities of the implant trial 112 may be further enhanced since it may be less restricted by size and power limitations. For example, the implant trial may include impedance sensing and pressure sensing with higher density of sensors while the implant may only include the array of electrodes for impedance measurement 132.

Figure 18:
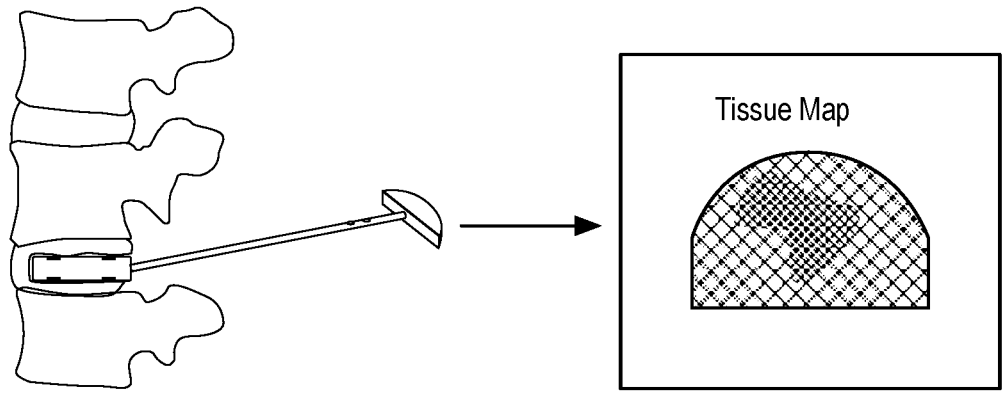
Figure 18:
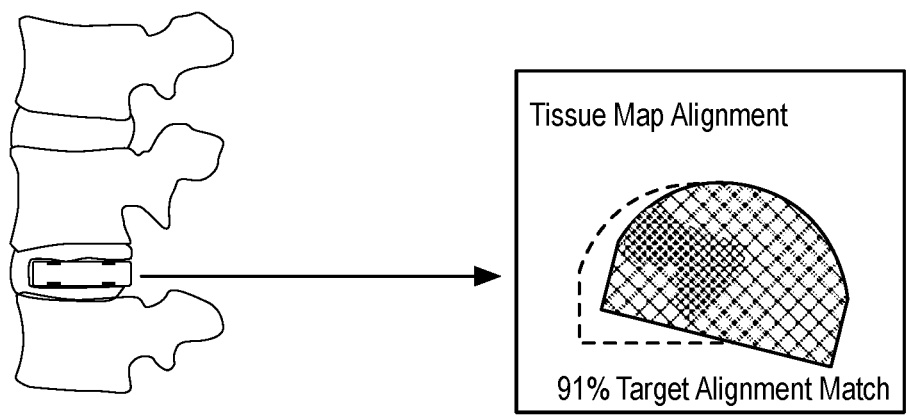

As a more detailed description of such a variation, the system may include an enhanced implant trial system and a medical implant system that cooperatively supply adjacency and orientation data to an implant feedback system. The enhanced implant trial system can include an implant trial body 112; a coupled arm attachment 120, a first sensor system 130 integrated into the implant trial body 112; a first sensor processing control system 140 communicatively coupled to the first sensor system 130, the processing control system 140 configured with instructions that when executed cause the sensor processing control system 140 to collect a first set of sensor data from the first sensor system 130 and generate a first set of adjacency data from the sensor data; and an implant feedback system 150 that updates state based in part on the adjacency data. The medical implant system can similarly include a medical implant body 114 (e.g., an orthopedic implant), a second sensor system 130 integrated into the medical implant body 114, a second sensor processing control system 140 communicatively coupled to the second sensor system 130, the second processing control system 140 configured with instructions that when executed cause the sensor processing control system 140 to collect a second set of sensor data from the second sensor system 130 and generate a second set of adjacency data from the sensor data. As shown in FIG. 18, a tissue map could be generated by an implant trial system and this could be matched to the current tissue map of a medical implant so that tissue alignment could be matched. The variation can include an implant feedback system 150 that is configured to present a comparison of the sensor data from the implant trial body 112 and the sensor data of the second implant body (e.g., a medical implant body 114) during use of the second implant body.

The sensor data could be adjacency data and/or orientation data. In one variation, the implant trial and the medical implant may both include orienting systems 136 configured to report the orientation of the implant bodies during use. The feedback system will preferably report a comparison of the orientation of the medical implant body 114 to the orientation corresponding to the implant trial body 112, which may additionally be associated with the tissue adjacency data.

The implant feedback system 150 may have many variations. In one preferred variation, the implant feedback system 150 is implemented as a user interface or more specifically a graphical user interface that is configured to display graphical feedback from the system. In one variation, the adjacency data is a sizing map, which is displayed in the graphical user interface. The sizing map can represent the spatial attributes of the tissue in adjacent to and surrounding an implant. This could be useful when displayed using an implant trial or for a medical implant (during surgery or post surgery).

In other variations, the implant feedback system 150 can be implemented to integrate with another system. The other system could be another body imaging system so that adjacency data can be synchronized with additional imaging data. In some variations, the adjacency data can be communicated to a robotic surgery system that can use the adjacency data as an input driving an automated surgical procedure performed by the robotic surgery system. Accordingly, the robotic surgery system can be at least partially controlled based on the adjacency data. For example, a doctor or the robotic surgery system may insert a sensor-enhanced implant trial into an extracted cavity, and then using that implant trial to perform refining extraction of tissue from the cavity based on sensed dimensions, tissue type, and/or other factors.

These above variations serve as representative examples of variations of the system and do not limit the system to these variations. Other variations and combinations of features of the system described herein can additionally or alternatively be implemented. The below detailed descriptions are representative of various alternatives and the system is not limited to any specific feature or variation.

Figure 11:
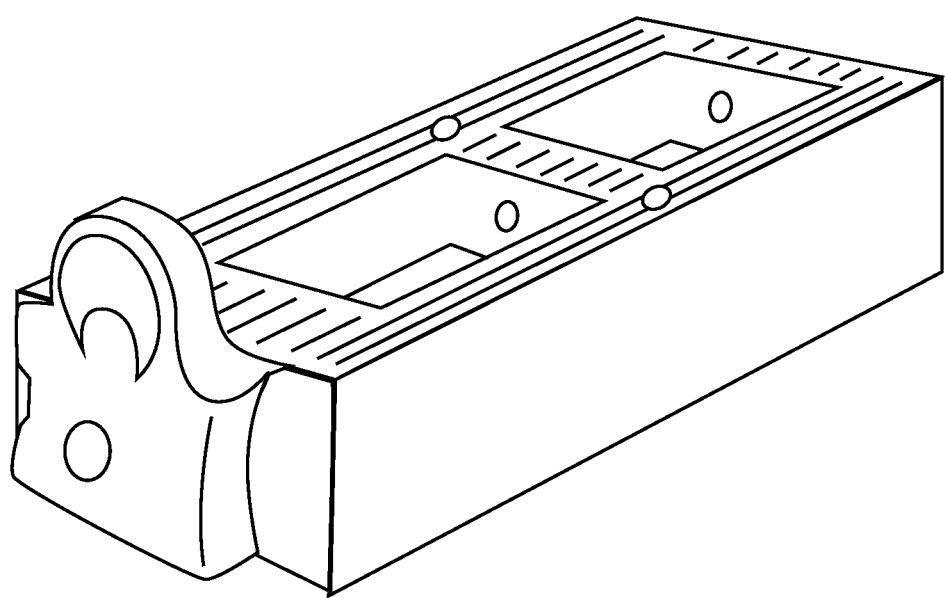
FIG. 11 is an image of an exemplary form factor of a surgical implant.

The implant body 110 of a preferred embodiment functions as the primary structural component of the implant such as the one described in U.S. patent application Ser. No. 15/075,152 filed on 19 Mar. 2016, which is hereby incorporated in its entirety. The implant body 110 can take the form of any suitable type of implant such as the lateral implant shown in FIG. 11. The implant body may alternatively be an orthopedic implant distinct from the one in U.S. application Ser. No. 15/075,152. The implant body 110 functions as the primary structural implant element. In many variations, the implant body may further function as an element housing, holding other implant subcomponents. In some variations, the implant body 110 is flexible. Alternatively, the implant body 110 may be semi-flexible or rigid.

The implant body 110 is preferably primarily composed of non-conductive material. In some preferred examples, the implant body no is primarily composed of polyether ether ketone (PEEK) polymer. Alternatively, the implant body 110 may be primarily composed of UHMWPE, PTFE, PAI, PPS, PA46, PA66, carbon fiber or any other non-toxic, non-conductive compound. Alternatively, the implant body no may be composed in part with engineered tissue, natural or synthetic (e.g. bone material).

In some preferred variations, the implant body no is partially conductive (e.g. partially constructed of titanium). In these variations, mechanical/structural elements of the implant body no may have electrical properties. In some preferred variations, some part(s) of the implant body no may function as an electrode. This electrode functionally is preferably in conjunction with the plurality of electrodes 132. Such implant bodies no may additionally house some or all circuit elements necessary for the electrode functionality. For examples, the implant body 110 may house some or all circuit elements, PCBs, leads, antennas, etc., included as part of the implantable component.

In some preferred embodiments, the implant body 110 is a spinal implant, more preferably an interbody fusion cage (i.e. spine cage). The spine cage functions as a prosthesis to assist in spinal fusion. In preferred variations, the spine cage geometry is an extruded prism of some defined form, which generally has a continuous outline. The spine cage may be incorporated with many geometries including, but not limited to, anterior lumbar interbody fusion (ALIF) cages, transforaminal lumbar interbody fusion (TLIF) cages, eXtreme lateral interbody fusion (XLIF) cages, posterior lumbar interbody fusion (PLIF) cages, anterior cervical fusion (ACF) cages, lateral cages and/or other suitable types of spine cages.

Dependent on the desired implementation, the spine cage may include one or more graft windows, which can be defined as internal implant cavities of the spine cage. Dependent on implementation, the spine cage may have additional design features. Examples include: surface coatings, surgery tool attachment points, teeth or high friction like structures to reduce implant mobility in biological tissue, internal cavity space to house implant subcomponents, and/or other elements.

Figure 4:
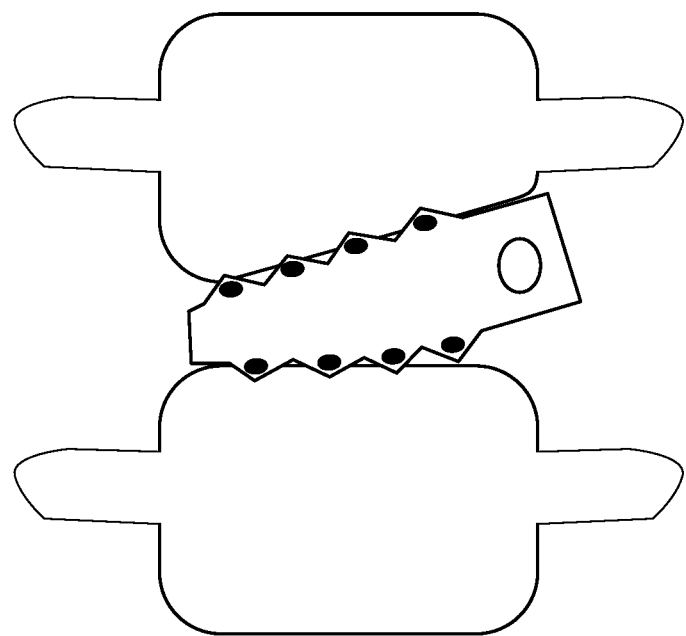
FIG. 4 is schematic representation of a system of preferred embodiment containing surface electrodes within implant protrusions.

As shown in FIG. 4, the implant body 110 may further include protrusions; i.e. extensions of the implant body that extends out from the implant body. The protrusions function as "non-smooth" surfaces of the implant body to effectively anchor the implant in place, to reduce implant mobility. Additionally, the protrusions may contain surface electrodes and function to aid and/or allow impedance measurements in adjacent tissue. Implant body protrusions may be singular shapes (such as the triangular protrusions shown in FIG. 4) that jut out of the body implant, but may alternatively comprise of a multitude of protrusions placed regularly, or irregularly, along the surface of the implant body. Examples of protrusion geometries include spikes, rectangular solid protrusions, or any other desired type of geometries. The protrusions may be sharp teeth-like extensions that embed themselves in adjacent tissue, but may additionally or alternatively be rounder shaped extensions that distend or displace adjacent tissue. In one variation, wherein the geometry of the adjacent tissue (e.g. bone tissue) is well known, the implant body no surface body may be customized such that the protrusions that complement and fit in to the tissue. For the preferred spine cage variation, the spine cage protrusions comprise rigid teeth-like protrusions on the upper and lower surface of the implant body no.

As discussed, in some variations, the implant body 110 is an implant trial body 112 which functions as a test implant for sizing the tissue cavity and an appropriate medical implant. The implant trial body 112 is a non-functioning structural replica of a medically functioning implant body that is generally not intended for implantation. The implant trial body 112 functions as a test object utilized to determine the appropriate implant size and shape for a specific patient. The implant trial body 112 may be used during a preliminary sizing and planning stage of a surgery, and is preferably used to determine the size and shape of a functional medical implant. A user/doctor may determine the correct implant body no size and shape by attempting to position implant trial bodies into the patient. Once the correct implant size is determined, the user may then use a functioning implant body no, of the appropriate size and shape, to implant into the patient. The enhanced implant trial variation of the system can provide unique capabilities to more accurately and consistently evaluate an extracted cavity and needed size for an implant.

Figure 12:
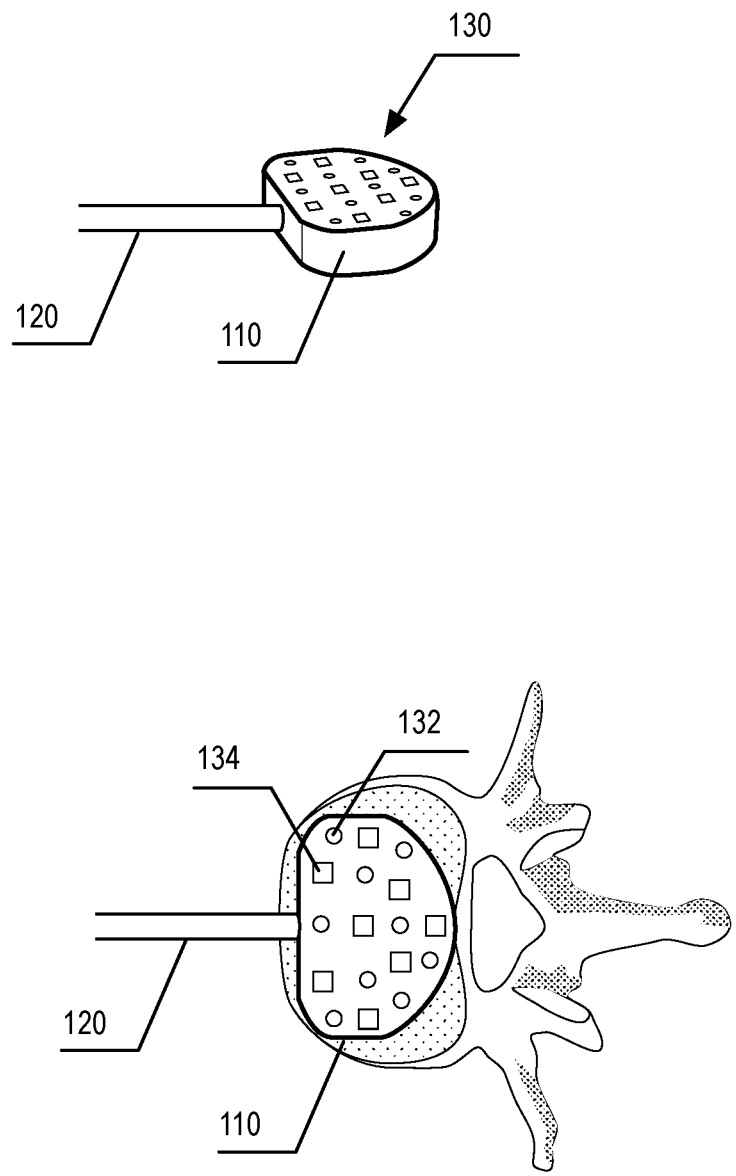
FIG. 12 is a schematic representation of an implant trial variation of the system.
Figure 13:
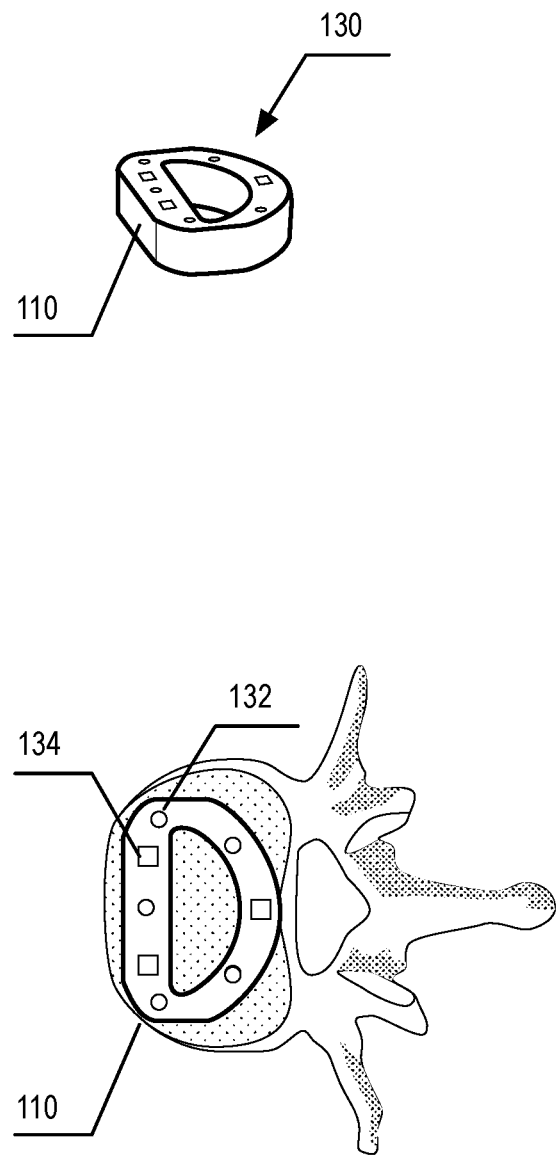
FIG. 13 is a schematic representation of a medical implant variation of the system.

The implant trial body 112 will preferably be sized and/or shaped in a form substantially similar to one of the medical implant bodies. For a spine cage, the trial implant body could be shaped similar to an ALIF cage, TLIF cages, XLIF cages, PLIF cages, LLIF, OLIF, ACF cages, and other similar cages. In some variations, the implant trial body 112 may not fully conform to the shape and form of a corresponding medical implant. For example, a defined through channel of a spine cage (as shown in FIG. 13) may be solid in an implant trial body 112 (as shown in FIG. 12). Sensors can be placed in this region of the trial implant body 112 such that tissue sensing can be performed on this region.

In some preferred variations, the system includes an arm attachment 120. The arm attachment 120 may function to enable easier positioning of the implant body 110 during surgery. The arm attachment 120 is preferably a long, slender, rigid structural component that firmly connects to the implant body no, enabling a user to better move and place the implant body through manipulation of the arm attachment.

Figure 5:
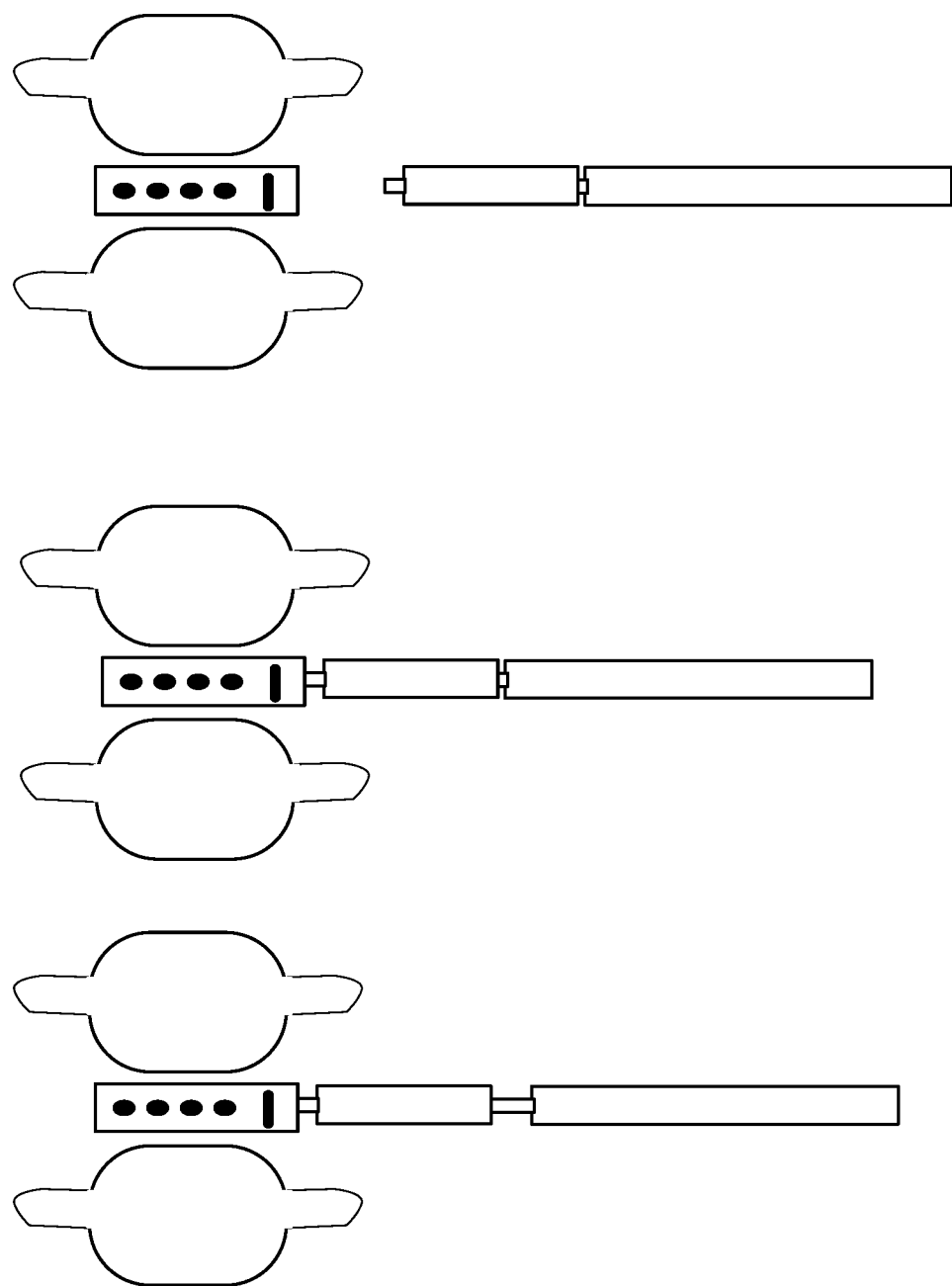
FIGS. 5 and 6 are schematic representations of a functional medical implant with a detachable arm attachment.

The arm attachment 120 may be utilized with an implant trial body 112, as shown in FIG. 5, wherein the arm attachment detaches from the implant body 110 Alternatively, the arm attachment 120 may be utilized with a medical implant body 114, in particular if the arm attachment 120 can be decoupled during surgery. The arm attachment 120 preferably extends from and physically couples to the implant body. The arm attachment 120 connects to the implant body along a face of the implant body 110 that would typically be exposed during surgery (e.g., the backside of the implant body). The arm attachment 120 may be made of any strong non-toxic material, such as certain types of stainless steel and carbon fiber. In some preferred variations, the arm attachment 120 may further have the ability to connect and disconnect from the implant body (for example, by screwing the arm attachment 120 into the implant body or by a magnetic end of the arm attachment connecting to a magnetic section of the implant body).

The arm attachment 120 preferably includes a hand grip and an elongated shaft. The hand grip functions to facilitate manipulation of the implant body no using the arm attachment. The elongated shaft extends from the hand grip to couple to the implant body no. The hand grip may be of any desired form. In preferred variations, the hand grip is significantly thicker than the body of the arm attachment. The thickness of the hand grip is preferably sufficient to enable a user to comfortably hold the hand grip. Preferably, the hand grip is sufficiently long to hold with a single hand (e.g. greater than 10 cm). In another preferred variation, the hand grip is sufficiently long to hold and manipulate with two hands (e.g. 30 cm). In some variations, the hand grip may have extending segments to aid in manipulating the arm attachment in a rotational motion orthogonal to the main body of the arm attachment, i.e. aid in screw/twist like motion of the arm attachment.

In some preferred variations, the hand grip has a rough surface with increased friction. Increased friction may function to provide improved grip to a user. The rough surface may be implemented in any desired fashion. Examples of how a rough hand grip may be implemented include: having a superficially etched surface of the hand grip, taping the hand grip with removable grip tape, or constructing the hand grip with a polymer.

In some preferred variations, particularly when constructed from a polymer, the hand grip may create an internal cavity. The internal cavity of the hand grip may enable placement of desired components, e.g. sensors, antennas, PCBs, batteries etc. Additionally, the internal cavity may enable customized weight alternation of the arm attachment for an improved user personalization. That is, weight components may be added, or removed, from the cavity of the hand grip to alter the weight and balance of the arm attachment.

Figure 6:
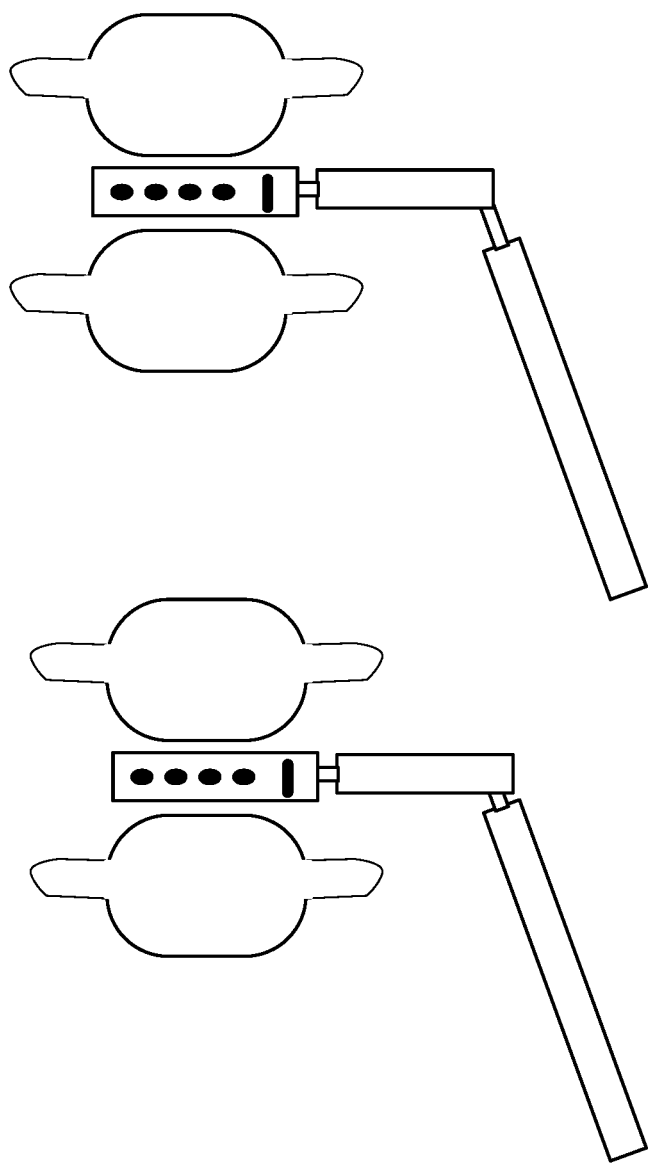

The arm attachment 120 preferably has a lean elongated rigid body. The lean elongated rigid body functions to provide greater stability while manipulating the implant body 110 with minimal interference to vision and surrounding tissue. In one preferred variation, the arm attachment 120 is a fixed rigid shaft statically coupled to a trial variation of the implant body 110. In a second preferred variation, the arm attachment 120 may have a hinge such that the arm attachment 120 may be fixed in a specific angle with respect to the implant body no. Preferably, the hinge mechanism has a locking mechanism such that the arm attachment 120 is fixed, once the locking mechanism is activated. FIGS. 5-6 show the schematic for one implementation of an arm attachment 120 with a hinge and a locking mechanism.

A removable arm attachment 120 can be used so that the arm attachment can be reused across different functional or implant trial bodies 110. The arm attachment 120 may include a mechanical or electrical input element that an operator can use to engage and disengage the arm attachment 120 from an implant body. Alternatively, the arm attachment may have a screw like connection. That is, the arm attachment may be attached or detached from the implant body no by "screwing-in" or "screwing-out" the arm attachment.

Figure 7:
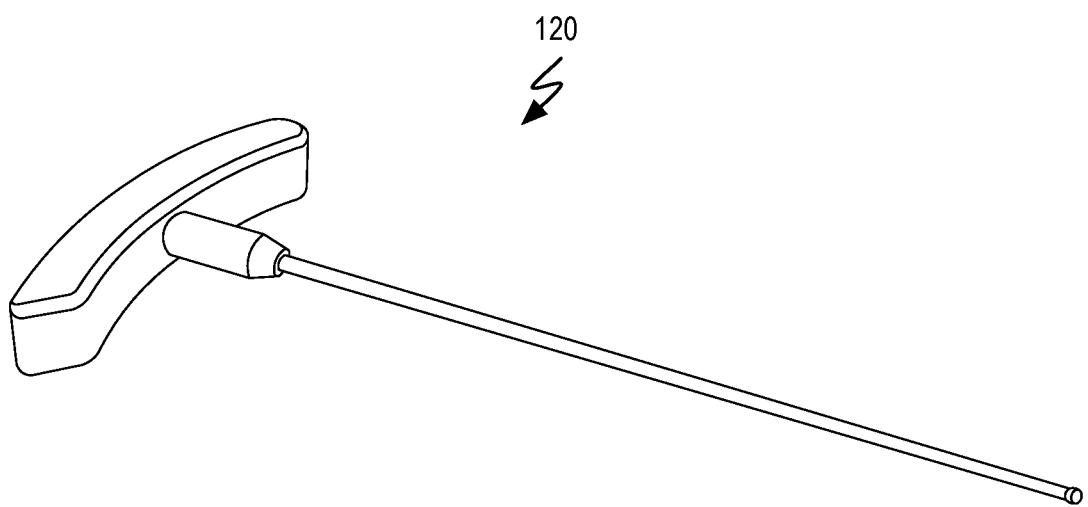
FIG. 7 is an image of an arm attachment of a preferred embodiment.

A surgeon may use the arm attachment 120 across a set of different types of implants of varying size and shape to identify the implant with appropriate size and geometry. FIG. 7 shows an image of an arm attachment that may be used with multiple implant trial bodies. The set of implant trial bodies may include one or more types of sensor-enabled implant bodies 120 described herein. These different types could be of different sizes, different cage types (e.g., ALIF, TLIF, etc.), and/or have different sensing capabilities. Depending on the current need and patient a doctor or other medical personal could select an appropriate implant trial. The attached implant body could be changed during a surgery and/or between patients.

In variations where an arm attachment 120 is used with a functioning medical implant body 114, the arm attachment 120 may be detachably connected to a medical implant body 114. During surgery, the arm attachment 120 may be used to manipulate and position the medical implant body 114. After positioning the implant body 110 to the desired location, the arm attachment 120 may be disengaged from the implant body. In this variation, an attachment mechanism can be mechanically disengaged either through a mechanical activation or through an actuation mechanism (electronically or pneumatically controlled). For example, a grip lever may couple through a clasp attachment mechanism such that manipulation of the grip lever (e.g., pressing, pulling, lifting the grip) opens the clasp allowing the arm attachment 120 to disengage and be removed from the medical implant body 114.

In alternative variations comprising the arm attachment 120 with an implant trial body 112, the arm attachment may be permanently fixed to the implant trial body 112. That is, the arm attachment 120 may be rigidly connected and integrated with the implant trial body 112. Multiple arm attachment 120s, each fixed to a different type of implant body of varying size and shape, may be used to identify an implant with appropriate size and geometry.

In some variations, the implant feedback system 150 or a type of feedback system can be integrated into the arm attachment 120. The user interface integrated into the arm attachment 120 could be graphical, light-indicators, audio, or tactile feedback system to convert adjacency data or information from the implant to feedback to the user. Sensor data of the sensor system 130 may be converted into a metric or discrete classification that provides a signal to an operator conveying the sensed state of the implant body. The feedback output could be a rating of fit compatibility, the percentage of desired surface coverage of the desired tissue and/or undesired tissue. In one example, the arm attachment 120 may have a graphical display and/or one or more indicator lights that activates in response to feedback output. In another example, the arm attachment 120 may generate audio tones from an audio feedback system (e.g., a speaker) based on the sensor data.

Figure 19:
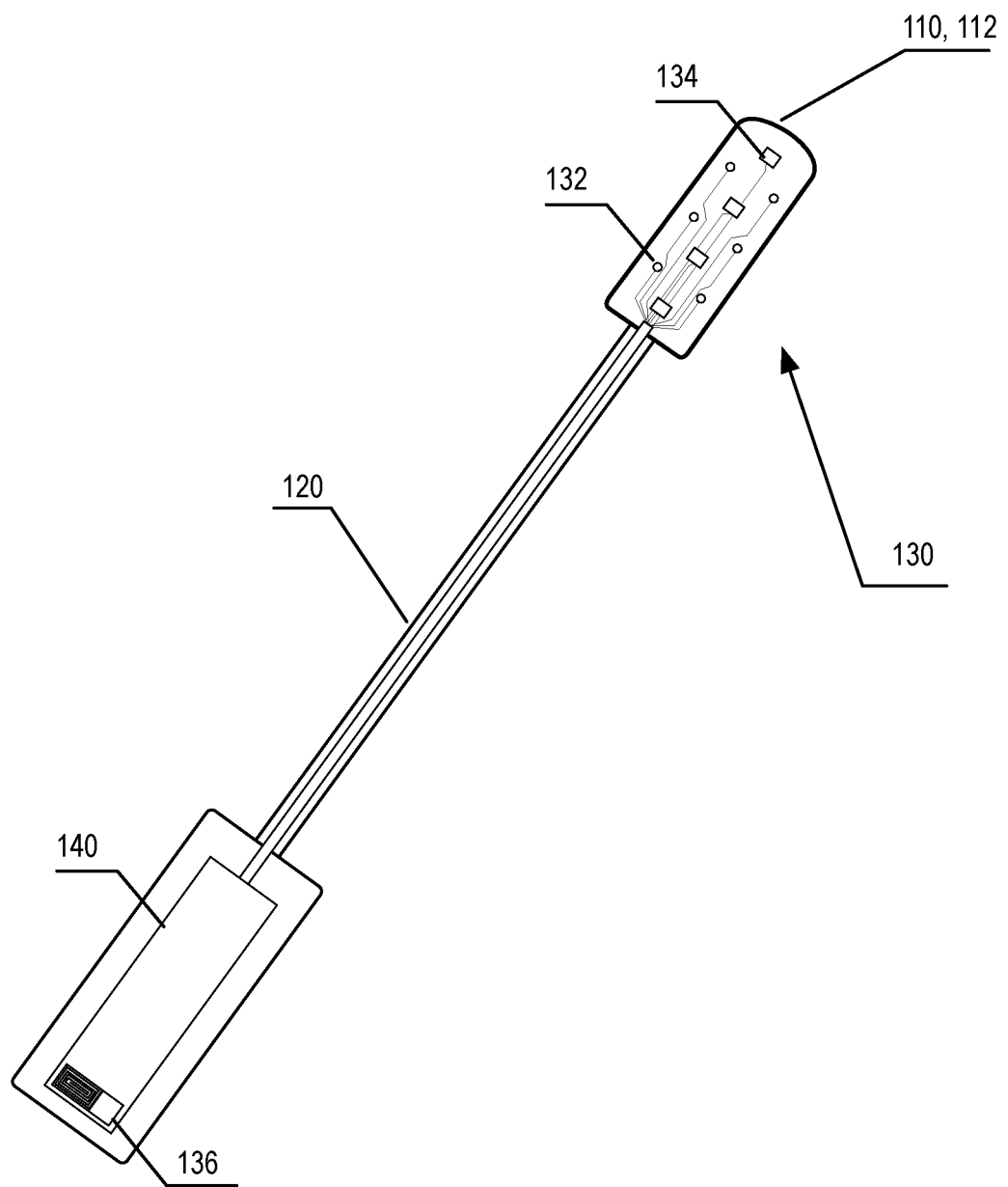
FIG. 19 is a schematic representation of an exemplary implementation of an implant trial variation of the system.

The arm attachment 120 may additionally house all or a portion of electrical components used to operate a sensor-enabled implant. For example, the arm attachment 120 may house at least a portion of the sensor processing control system, the power system, communication modules, and/or other electrical components within the hand grip (i.e., the handle) of the arm attachment. Electrical connections may run the length of an elongated shaft to conductively couple to the electrical components (e.g., the sensor sub-systems) within the implant body 110 as shown in FIG. 19. In some variations, an orienting system like an antenna, an IMU, and/or other orienting system elements may be integrated into any suitable part of the arm attachment 120 instead of the implant body no. Because the orientation and position of the implant body no can preferably be determined relative to the arm attachment 120, the orienting system can alternatively be housed in the arm attachment like the antenna shown in FIG. 19. In the case of an implant trial body 112, the arm attachment 120 may expand the physical space in which a battery, sensing circuitry, and/or processing systems can be housed. In some variations, some or a portion of the processing and data interpretation may be performed through a remote computing system. In a similar manner, the arm attachment 120 may be used as housing for electrical connections to the sensor system 130.

The sensor system 130 of a preferred embodiment functions to gather functional data with regards to the conditions external to the implant body no and/or implant position. The sensor system 130 may include one or more different types of sensing capabilities. The sensors sensing external state in proximity and adjacent to the implant body can be used in generating adjacency data. In this variation, sensors of one kind or another are distributed across the surface of the implant body. Multiple sensing points are preferably used so that multiple sample points can be collected such that a map of the conditions can be formed. The sensor system 130 may include one or more of a plurality of electrodes 132 used for impedance measurement, pressure sensors 134, and/or an orienting system 136. Additionally or alternatively, the sensor system 130 may comprise other sensors and sensor systems. Examples of possible sensors that may be implemented with the sensor system 130 include: temperature sensors, pH sensors, imaging sensor, and/or other types of sensors. The type of sensors included with the sensor system 130 preferably depends on the desired implementation.

The plurality of electrodes 132 of a preferred embodiment functions as sensing points for performing impedance measurements. The plurality of electrodes 132 are preferably positioned within the implant body such there is at least one exposed region on the surface of the implant body for each electrode of the plurality of electrodes. An array of electrodes is preferably positioned across each face or surface of the implant body 110 for which impedance measurements are desired. The impedance measurements are preferably used to determine or predict tissue type or state. In spine cage variation, the tissue above and below the cage is of significant importance. Accordingly, the plurality of electrodes may include a subset of electrodes positioned on a first external face of the implant body (e.g., a top face) and a second subset of electrodes positioned on a second external face of the implant body (e.g., the bottom face). The first and second external faces are on opposite sides of the implant body. For example, there may be six electrodes on the top face and six on the bottom face of a spine cage. By collecting multiple impedance measurements above and below the implant body, a map of tissue classifications can be mapped for the first and second external faces and presented through the feedback system 150

The electrodes are preferably used for collecting impedance measurements of tissue adjacent to the implant body 110, which can be used to determine the composition of surrounding tissue. In these variations, electrodes may be positioned on the surfaces of the implant body 110 to detect the material composition of adjacent tissue. Once an implant body 110 is placed in some position in the body of a patient, an impedance measurement across a pairs of single or multiple surface electrodes may determine the composition of the adjacent tissue. In some preferred variations, the impedance measurement of surface electrodes can determine if a surface of a spinal implant is adjacent to a vertebra. The surface electrodes may alternatively determine adjacency to other tissue, such as muscle, fat, or connective tissue. This may be used in a trial variation to determine if the extracted cavity is properly prepared. For example, impedance measurements may be used to measure the presence and/or thickness of cortical bone above and below the implant body 110 to determine the state of the endplate (Cortical bone, the harder outer layer of bone, has a higher impedance than the softer trabecular core). Another example is to use impedance measurements to measure the degree of bleeding from the endplates (blood normally has a lower impedance than bone) and/or or the presence of a disc adjacent to the implant body 110 along any surface.

As one exemplary application this sensing capability can be used by a user interface to present a map of tissue on select surfaces surrounding an implant body. The map could graphically present tissue classification by location to inform a surgeon or possibly an robotic or automated surgical tool. In another variation, impedance measurement can establish a map of tissue type that can be used in monitoring position of an implant during surgical insertion and afterwards. The existing bone structure can be used as a reference for determining the position of the implant relative to a bone formation. Periodic checks may be used to detect implant displacement and drift.

When performing impedance measurement, a sequence of impedance measurements is made across multiple pairs of electrodes. During an impedance check, the impedance measurement related configuration of the sensor processing control system 140 can be configured to cycle through a set of impedance checks so that impedance can be measured in different regions around the implantable component. Preferably, impedance can be measured in substantially all the surrounding area of the implantable component. However, some variations may only be configured for measuring impedance in particular regions.

In one variation, the pairs of electrodes can be preconfigured such that each electrode when used for sensing impedance has a consistent polarity. In another variation, the polarity can change. Control circuitry cycles through activating pre-configured pairs. In another variation, one or more electrodes may be configured for use as an electrode for multiple electrode pairs. For example, one electrode may be used as an anode (or cathode) for electrode pairs of the electrodes surrounding that electrode. The plurality of electrodes can be individually controllable such that independent impedance measurements can be made for multiple pairs. In one implementation, the plurality of electrodes 132 is connected to circuitry for activating simulation through a set of multiplexers such that impedance could be selectively measured between any two (or more electrodes).

A implant trial may include a plurality of electrodes with a different configuration compared to a medical implant. The density and number of electrodes could be greater in an implant trial as shown in FIGS. 12 and 13 since the implant trial may have less space and energy limitations. Additionally, in an implant trial variation, the implant trial body 112 may not have a defined cavity where a medical implant body 114 does. Instead, the implant trial body 112 can include electrodes and sensor elements in a surface region where a cavity is defined in a medical implant.

The electrodes may additionally or alternatively be operated in an orienting mode, wherein a subset of electrodes function as a position sensing mechanism. Preferably, the electrodes may be used to measure impedance in the space around and within the implant, thereby determining implant positioning and implant alignment with respect to proximal tissue (e.g. bone, nerve tissue, etc.). The system preferably uses this orienting mode to provide positioning and alignment assistance during surgery. In the case of an implant trial and possibly in some functional medical implant variations, the primary objective of the electrodes may be for sensing.

In one preferred variation, the plurality of electrodes 132 is composed of titanium electrodes. Additionally or alternatively, the plurality of electrodes 132 is composed of platinum electrodes. Generally, the plurality of electrodes 132 is composed of any electrically conducting non-toxic material. In some variations the electrodes may be composed of different types of material. Dependent on functionality subsets of electrodes may have different compositions. In some variations, the electrodes may be composed of multiple materials. For example, in one variation, a subset of electrodes from the plurality of electrodes 132 is composed of one layer of titanium and one layer platinum. This multilayer composition may function to allow improved functionality. For example one layer may be used as a cathode and the other layer may be used as an anode. These multilayer electrodes preferably have an insulation material between the two layers to electrically isolate them. Multilayer electrodes may enable the creation of more complex electric fields. For example, a single electrode functioning as a cathode and an anode may potentially create a localized electric field around itself.

An electrode of the system may be further generally defined as any material that can hold charge and is given the capability to polarize, such that the electrode may function as a cathode or anode of a circuit, allowing current to flow. Electrodes may be thin wires with at least a portion of exposed conductive surface, but may alternatively be of any arbitrary size and/or shape as required by the system. Examples of electrodes may include, but are not limited to: exposed conductive pads, a ring or band, a conductive structure that has exposed conductive surfaces across a defined 3D space, and/or any suitable type of form. Electrode size, shape, and position may be dependent on the body implant and the desired patient treatment. Individual electrodes may have different configuration across an implant.

Conductive connections to the electrodes are preferably made internally within the implant body 110. Wires or other conductive connections are preferably embedded within the implant body and shielded from the external surface of the implant body no. The conductive connections preferably connect the electrodes to any associated circuitry, which may be part of the sensor processing control system or other forms of control circuitry used in activating the electrodes.

The plurality of electrodes 132 (especially for a medical implant variation) may serve additional purposes. In one orthopedic implant variation, the electrodes may provide electrical stimulation like the plurality of electrodes 132 described in U.S. patent application Ser. No. 15/075,152 filed on 19 Mar. 2016, which is hereby incorporated in its entirety. The electrodes, which make up the plurality of electrodes 132, function to hold charge that would thereby create one or more electric fields. In preferred variations where the implant body is a spine cage, the plurality of electrodes 132 that may additionally function to create electric fields that may induce bone growth, osteogenesis, or bone breakdown, osteolysis. The electrodes of a functional medical implant may be used to promote osteolysis and/or osteogenesis through electrical stimulation while implanted in the body of a patient.

Subsets of the plurality of electrodes 132 may function dynamically and distinctly. That is, a subset of the plurality of electrodes 132 may function as negatively charged electrodes, while another subset of the plurality of electrodes may function as uncharged electrodes (inactive), and another subset of the plurality of electrodes 132 may function as positively charged electrodes, wherein any of the subsets of the plurality of electrodes may contain, all, some, or no electrodes. Electrode functionality may be dynamically modifiable. That is, each subset of electrodes may have their activation state modified or completely changed as desired. For example, an electrode may be switched between an anode-state, cathode-state, and neutral state. Additionally or alternatively, an electrode, or subset of electrodes, may continue to function in the same state but the charge/polarity of the electrode may increase or decrease as desired. Although any, and/or all subsets of electrodes may function independently, electrode functionality of subsets of electrodes preferably function to maintain a polarity that counter-balances the polarity of other subsets of electrodes. Alternatively, a subset of the plurality of electrodes may have another polarity (or no polarity) for other functional reasons. For example, one subset of the plurality of electrodes may counterbalance another subset of the plurality of electrodes to a greater or lesser degree, allowing for net positive or negative fields to modify osteolysis and osteogenesis as desired. In preferred variations, a new subset of electrodes from the plurality of electrodes may be added or removed dynamically as seen necessary. Additionally, in preferred variations, electrodes from the plurality of electrodes 132 are preferably added and/or removed from any given subset of electrodes dynamically as seen desired. Furthermore, functionality of any subset of electrodes can preferably change dynamically as seen necessary. In alternative variations, the functionality of some and/or all electrodes in the plurality of electrodes 120 is fixed.

Electrode positioning may be used to designate regions of preferred bone growth and/or bone decay. In various implementations, the implant body 110 may also include integrated electrode sites, which may be distributed across the geometry of the implant body in such a way as to facilitate bone growth and/or decay in distinct regions. For example, in certain variations, electrodes may be placed along or near the top and bottom surfaces of a spinal implant body to induce bone growth and bone fusion with the adjacent vertebrae, electrodes may be placed directly outside of the implant body to prevent bone growth on the exterior of the implant, or electrodes may be positioned as discs along the implant body interior surface to induce rings of bone growth and/or bone decay. In some variations, electrodes may be placed on the surfaces of defined cavities of the implant body no to induce bone growth in the implant body cavity. In one preferred variation, the implant body 110 comprises a spine cage with eight electrode conducting pads. In this embodiment each long side of the electrode, two electrodes are exposed on the exterior surface and two electrodes are exposed on the interior surface.

Figure 14:
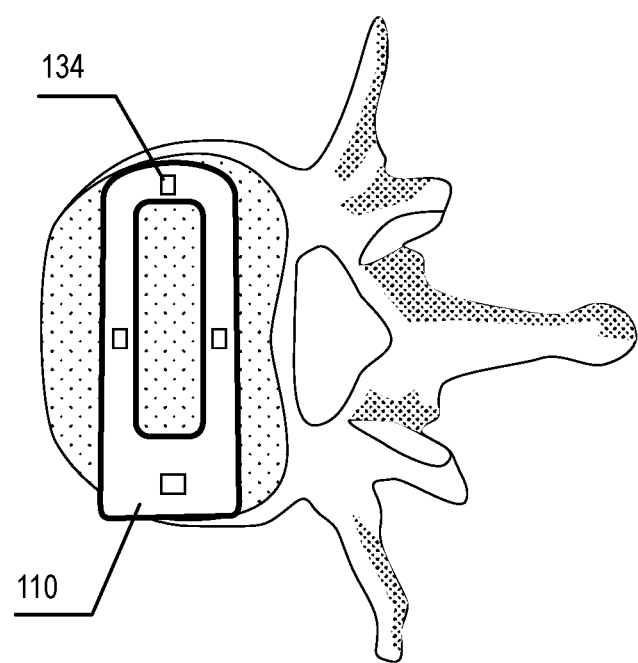
FIG. 14 is a schematic representation of a variation with pressure sensors as the sensor system.

In some preferred variations, the sensor system 130 includes a plurality of pressure sensors 134. Pressure sensors 134 function to measure pressure on the surface of the implant. In connection with a set of pressure sensors, the sensor processing control system can include instructions to generate sizing map based in part on pressure data collected from the pressure sensors 134. This may be used in combination with tissue classification to make a sizing map of adjacent tissue, which can show both dimensional information and the type of tissue at different regions. Alternatively, the sensor system may include only one sensor sub-system such as the pressure sensors 134 as shown in FIG. 14 or any other suitable sensor sub-system. The sizing map can be a spatial mapping of tissue pressure across the external surface of the implant body 110. This spatial mapping may be classified or presented to represent sub-regions of extracted tissue surrounding an implant body no that are under-extracted and/or over-extracted. Under-extracted may be characterized by extra or additional pressure above a maximum pressure threshold. Over-extracted may be characterized by reduced or lack of pressure such that the pressure is below a minimum pressure threshold. The maximum and minimum pressure thresholds may, in some implementations be the same threshold, but are preferably different to define a range of acceptable pressures. By measuring the pressure on the surface of the implant, the system may leverage pressure data to improve the positioning of the implant and to detect the type of tissue in contact with the implant. In preferred variations for a spine cage, at least one pressure sensor 134 may be positioned on the top and at least one pressure sensor is positioned on the bottom surface of the implant body 110, as shown in FIG. 3. In preferred variations, an array of pressure sensors 134 across the surface of the implant body 110. In a preferred variation, a subset of pressure sensors are positioned on a first external face of the implant body and a second subset of electrodes are positioned on a second external face of the implant body, where the first and second external faces are on opposite sides of the implant body 110. For example, pressure sensors can be positioned on both the top and bottom of the implant body 110 to enable a pressure mapping of both surfaces. As part of an implant trial, the pressure sensors 134 may improve the size determination of the appropriate implant size. As part of a functioning implant, the pressure sensors may aid in monitoring pressure buildup on the implant body 110 surface and/or changes in pressure on the implant, and potentially detect inappropriate implant motions (e.g. if the implant body 110 is drifting or slides out of vertebral column). Pressure sensors may also be used to determine the expected stress on the graft in the graft window and predict the eventual stress on the bone in the graft window.

The pressure sensors can be strain gauge based, capacitive pressure sensors, piezo-resistive pressure sensors, and/or any suitable type of pressure sensor. As with the electrodes, conductive connections to the sensors are preferably made through connections embedded within the implant body 110.

In preferred variations, the orienting system 136 is a component of the sensor system 130. The orienting system 136 is preferably comprised of an implantable orienting component, preferably connected to the implant body 110; and a non-implantable orienting component, comprising circuitry external to the patient. The orienting system 136 functions to determine the orientation of the implantable orienting component with respect to the non-implantable orienting component, and thus determining the orientation of the implant with respect to the non-implantable orienting component. The orienting system 136 may additionally or alternatively determine the distance and position of the implantable orienting component with respect to the non-implantable orienting component.

In some preferred variations, the sensor system 130 includes an orienting system 136. The implantable orienting component functions to detect orientation of the implant body no. This is preferably done when an implant body is positioned by a surgeon, but could also be used in measuring orientation post surgery. In one variation, the orienting system 136 includes one or more sensor that can measure orientation such as an inertial measurement unit (IMU), an accelerometer, or a gyroscope. The orientation from such a sensor can be read and communicated for processing by the sensor processing control system 140. Such a sensor based approach may be used for an implant trial variation where space and power considerations may be less limited.

Figure 15:
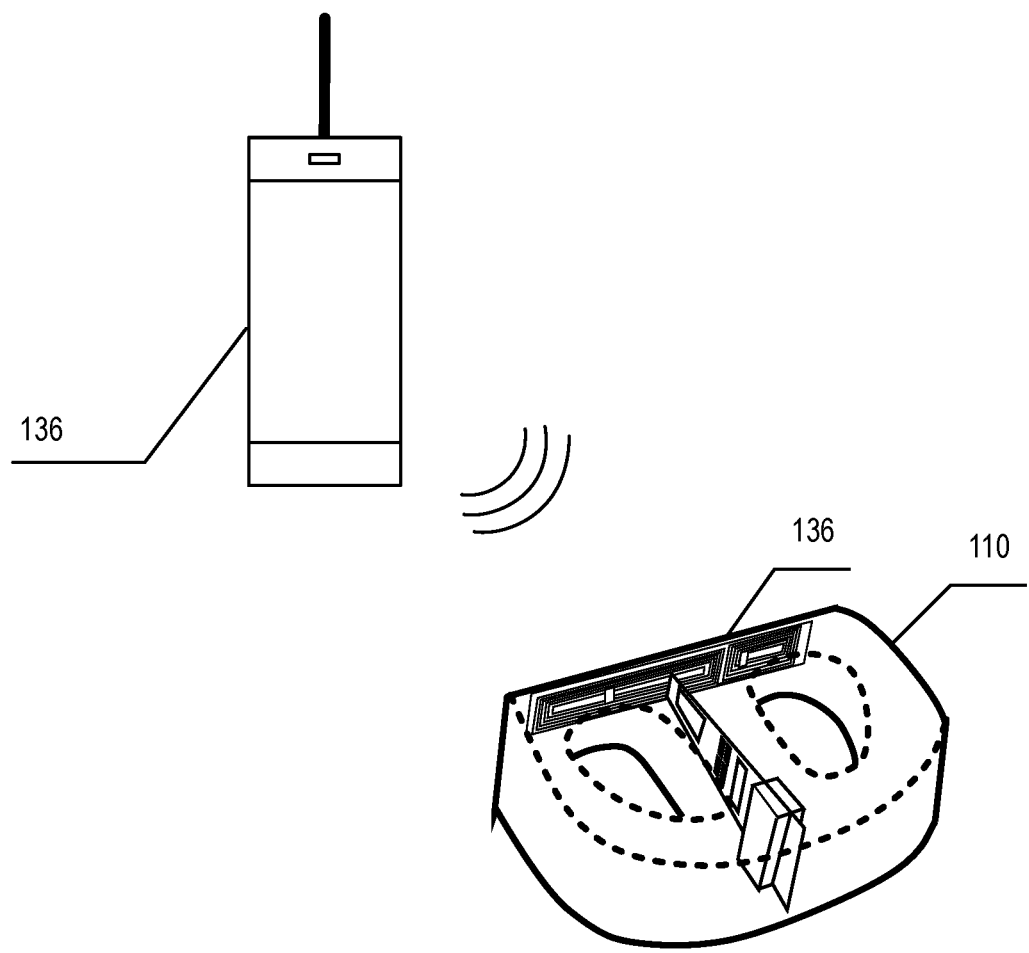
FIG. 15 is a schematic representation illustrating integration of an antenna in an implant body as part of an orienting system.

In another variation, an oriented object fixed to the implant body can enable detection of the implant body orientation. The orientation can preferably be remotely detected or inspected using an external non-implantable portion of the orienting system. In one preferred variation, the orienting component would be an antenna as seen in FIG. 15. This variation may be more useful for a medical implant variation, where a dedicated sensor may not be practical, and where there exist other components of the medical implant variation that can be dual used for detecting orientation such as an antenna for wireless power transmission and/or data communication. The implantable orienting component may have any desired size and/or shape limited only by available space. Examples of shapes for an implantable orienting antenna include: a line, parabola, disk, coil, or any other oriented antenna. The implantable orienting component may be a distinct orienting system component, but may alternatively be a system component with dual-purpose role.

Examples of components that may play a dual-purpose role as the implantable orienting component include: electrodes, implantable communication components, implantable control components, or implantable power components. In some variations the implant body itself may function as the implantable orienting component. For example, the implant body may include an oriented metal casing. Energy powered through the metal casing may enable the casing to function as an oriented antenna that can be detected externally.

The non-implantable orienting component of this variation functions to detect the orientation of the implant body 110 with respect to itself. Additionally or alternatively, the non-implantable orienting component may detect the orientation of the implant body with respect to another known object. The non-implantable orienting component preferably can include an antenna, or an antenna array, that detects the orientation of the implantable orienting component (e.g., one or more antennas embedded in the implant body) through signals sent and received between the implantable and non-implantable orienting components. The non-implantable orienting component preferably detects signal strength from different regions of the implantable orienting component, thus detecting the orientation of the implantable orienting component and the implant body 110. Transmitted signals may be of any type of electromagnetic signal(s) that can penetrate sufficiently far through a biological organism and does not damage tissue. Examples of transmitted signals include, IR, or radio. The non-implantable orienting component may be a portable device that can be carried and/or a non-portable device that is at a relatively fixed orientation for the majority of its operation. In some variations both a portable and a non-portable non-implantable orienting component is implemented.

In one variation, the antenna or more generally the non-implantable orienting component may be actuated or moved. During an orienting function mode, the antenna can actuate across multiple directional positions. In the case of an antenna, the signal strength/coupling at the various positions, and/or directions, can be used in assessing orientation of implanted orienting component. In another variation, the non-implantable orienting component may include multiple orienting subcomponents. More specifically, the non-implantable orienting component can include multiple antennas with multiple orientations. The antenna array may be used in place of actuating or in combination with actuation. The antennas are preferably arranged and integrated into the implant body 110 at distinct positions and orientations. Preferable each antenna is aligned along a distinct axis and/or plane depending on the type of antenna and the signal strength spectrum over the antenna array may be used to determine the implant orientation. Additionally or alternatively, multiple antennas may be used in the implantable component to provide alternative signal coupling capabilities from the implant-side of the system. In an alternative variation, wherein the implantable orienting component is an IMU. During the orienting mode, the IMU may wireless transfer data on the position and orientation of the implant body 110 with respect to the earth.

The sensor processing control system 140 preferably controls some or all electronic components of the implant. The sensor processing control system 140 is communicatively coupled to the sensor system. The processing system is additionally configured with instructions and/or circuit implemented configuration that cause the sensor processing control system 140 to collect sensor data from the sensor system. The processing system can additionally generate adjacency data and/or orientation or position data from the sensor data. Adjacency data is preferably generated in variations where the information on the surrounding tissue is used. Orientation and position may be used to determine the current placement or a change in placement. The sensor processing control system 140 may be made of various subsystems used to interface with different sensor subsystems like the plurality of electrodes 132, the pressure sensors 134, and/or an orienting system 136.

The sensor processing control system 140 may additionally be part of control circuitry or a processor system used in controlling other aspects of the system like power management, communication, data storage, and the like. The sensor processing control system 140 preferably communicates or otherwise outputs data to the implant feedback system 150.

The sensor processing control system 140 may be implemented as a singular distinct system, which can be housed external to the implant body 110 such as in the arm attachment 120 or in an external device in communication with an implant (e.g. through wireless communication and/or wired). Alternatively, the sensor processing control system 140 may be comprised of multiple separate systems. There may be individual control systems for different sensor sub-systems. Additionally some processing and data communication and management could be performed in a separate device. In general some portion of control circuitry is directly connected to the sensor systems for collection of data from the sensors. Although, some variations with an orienting system may operate without control circuitry in the implant body 110 since an oriented component may be sensed remotely.

The sensor processing control system 140 may be located within a housing inside the implant body, or may be located in an external housing connected to the implant body. As a distinct system entity, the sensor processing control system 140 may be located outside of the body; or may include a combination of implantable and non-implantable components. The sensor processing control system 140 may have a processor allowing it to control each individual electrode distinctly, and/or subsets of electrodes as one group. The sensor processing control system 140 may additionally or alternatively include discrete circuit based systems configured to control the system. The sensor processing control system 140 may function autonomously, but may additionally, or alternatively, be controlled by a user through an external control device or communication system.

In a variation using the electrodes for impedance measurement, the sensor processing control system 140 can include an electrode control system configured to measure impedance across multiple pairs of electrodes from the plurality of electrodes. In this variation, configuration to generate adjacency data from the sensor data generates a map of tissue classifications from the impedance measured. More specifically multiple impedance measurements are collected from multiple pairs of electrodes in the plurality of electrodes. The different pairs measure impedance across multiple spans forming a representative image of the impedance of the tissue adjacent and in proximity to the implant body no. Impedance can have some correspondence to tissue type. In this way multiple impedance measurement from different locations can be used to create a map of tissue classifications.

This impedance mode of the sensor processing control system 140 may be used during a surgery stage and/or implant status check to assist or inspect installation, position, and proper alignment of the implant. During a post-surgical stage, the impedance-measuring mode may be used in assessing bone growth during the life of an orthopedic implant. Bone growth data may then be leveraged to dynamically adjust electrical stimulation control to modify bone growth/decay.

The sensor processing control system 140 may function to control the activation, current, charge, amplitude, and/or polarity of the plurality of electrodes. The sensor processing control system 140 can facilitate a systematic collection of impedance measurements. For example, the sensor processing control system 140 may allow current/voltage to be only applied at the surface of the electrode sites, thus allowing the distribution of current/charge density to be controlled by the placement of the electrodes as well as their state during impedance measurements. In an alternative variation, a subset of electrodes may be control isolated from a distinct subset of electrodes, or preferably control isolated from all other electrodes. In this variation, each set of electrodes, or each electrode, may be independently controlled by the sensor processing control system 140 such that the current/voltage in proximity of the implant may be partially or completed manipulated as desired.

In some medical implant variations, the electrodes may additionally be used for additional purposes such as supplying electrical stimulation. Accordingly some alternative implementations of the control circuitry may include a bone growth operating mode and configuration. The electrodes may be used to generate electrical fields to promote osteolysis and/or osteogenesis. In the bone growth operating mode, a control system can activate the desired electrodes to promote bone growth in desired regions. For example, for the spine cage variation, the sensor processing control system 140 may promote bone growth in the interior cavity of the spine cage while promoting bone decay at the exterior of the spine cage. Bone growth operating mode may function both autonomously (e.g. pre-programmed growth, or in response to current bone growth activity), or may be user controlled (e.g. by a medical professional, using an external control device).

In a variation using pressure sensors, the sensor processing control system can include configuration to collect pressure data from the pressure sensors and where generating adjacency data from the senor data includes generating a sizing map based on the pressure data collected from the pressure sensors. The location of the pressure sensors can be used along with the detected pressure data to form a map of pressure. As the dimensions of the implant body 110 are known, the pressure data may be used to form a relief map using the pressure as an estimate of offset from the implant body out surface. When the pressure sensors are only on particular faces or surfaces of the implant body, the sensor processing control system can generate a sizing map for those particular faces.

In a variation where an orienting system is used, the sensor processing control system 140 may include configuration to read orientation data from the orienting system. In the case where the orienting system includes an IMU, accelerometer, or gyroscope sensor, then orientation data can be read from the sensor and communicated. In some variations, the orienting system may involve the use of an external non-implantable component as described above to interrogate an oriented component of the implant. Orientation data from this variation may be communicated to the sensor processing control system 140 or directly to the feedback system 150.

The implant feedback system 150 functions as a system element for conveying sensor information to a user (e.g. user interface feedback for a surgeon or doctor) and/or a connected system (e.g., feedback data communicated to a body imaging tool and/or a robotic surgery tool).

When used in a user interface, the implant feedback system 150 can synthesize and convey relevant forms of senor data such as a map of tissue classification from an impedance map, sizing/fit information from pressure data, and/or implant orientation information from the orienting system 136. Additional or alternative sensor data may additionally be used.

In one variation, the implant feedback system 150 may be part of a graphical display system. The graphical display system may output a 2D or 3D graphical representation of the impedance map and/or the position relative to key body components. In another variation, the graphical display may output a 2D or 3D graphical representation of pressure data. As discussed the pressure data may reflect sizing information for an extracted cavity. As another variation, the implant feedback system 150 could be represented through a virtual reality system and/or augmented reality system. However, any suitable medium of user feedback can be used to convey position information.

The implant feedback system 150 may provide functionality during the surgical process of implantation and/or during "normal" implant activity after surgery. During the surgical process, the implant feedback system 150 may function in combination with the implant trial to provide the user with appropriate sensor data. For a surgical example, for a spine cage implant, the feedback system 150 may provide impedance data showing that the implant body 110 is adjacent to bone above and below (as desired), but the feedback system may additionally present pressure data that shows the top vertebrae is only placing pressure on part of the implant; which may then suggest to the user that the implant is positioned correctly but not of the correct size. For a post-surgical example, the implant feedback system 150 may provide impedance data showing bone growth in an undesired location (e.g. dorsal exterior of the implant). This information may then enable a user to make adjustments to change bone growth conditions.

A sizing map (e.g., map of pressure data) and/or map of tissue classification (e.g., map of impedance measurements) can be useful output of a trial variation. In some variations, they are combined to form a sizing map of adjacent tissue. From the sizing map, a surgeon could see regions that spatially need to be further extracted, have sufficient sizing, or have been cut back too far. The map of tissue classification can help so that the surgeon can appropriately deal with different type of tissue. For example, in spinal fusion surgery the disc is removed and so if the map of tissue classification indicates remaining disc material, the surgeon can go in and remove the disc material before inserting a medical implant.

The graphical display system may additionally or alternatively present information in other forms. The implant feedback system 150 could alternatively include other forms of visual, audio, and/or haptic forms of user feedback output. For example, various graphical indicators integrated into the system (e.g., into an arm attachment) may provide indications of discrete information such as "aligned", "near-alignment", and "not aligned" or any suitable forms of orientation/positioning state. The positioning feedback system preferably dynamically updates in real-time during surgery. A user (e.g., surgeon) can preferably use the positioning feedback system to determine when the implant size, position, and/or orientation are satisfactory. The implant feedback system 150 may alternatively be used during a checkup post-surgery to assess any changes to position/orientation in the body.

In one variation, the system can be used in matching the orientation of a medical implant to a target orientation determined by a sensor-enhanced implant trial. In this variation, the feedback interface can present feedback on the comparison of the current orientation of the medical implant to the target orientation. This may be based on comparing a detected orientation of an implant trial during an initial sizing procedure to the currently detected orientation of a medical implant. In another variation, the positioning guidance may be based on comparing adjacency data sensed from an implant trial during an initial sizing procedure to the currently detected adjacency data. This functions to map the sizing or tissue map.

In a variation, where the system is used for long-term monitoring of an installed implant, orientation and/or adjacency data may be periodically collected and compared. The feedback interface may show changes or variations. In particular drift or trends can be highlighted to show when an implant is moving out of position.

In one variation, the implant feedback system 150 may further include a camera system that functions to map visual body position with the implant system. In one variation, the arm attachment 120 or other element of the implant system includes a visual registration element such as an IR light to facilitate tracking of the implant system by the camera system. The camera system can be used to correlate implant position and orientation with body position using computer vision and pose estimation or other suitable techniques. In some variations, a body imaging system such as a CT scan, magnetic resonance imaging system, ultrasound system, X-ray, or other suitable imaging system can be used to integrate other body visuals for representing implant position. For example, if a CT scan of the trunk of a patient has been obtained, this can be used to visualize where the implant body 110 is positioned by using the camera system to map between the two systems.

In some variations, the implant feedback system 150 may be a data interface to another system that can use the generated data from the sensor-enhanced implant. As one example, the generated adjacency data detailing sizing dimensions and tissue classification can by communicated to a robotic surgery tool. Accordingly, some implementations of the system may include the robotic surgery tool. Though some implementations may include just an interface to a robotic surgery tool. The robotic surgery tool can be controlled in based on the adjacency data. The implant trial may additionally be coupled to a robotic surgery tool such that it can use the implant trial for sensing and then use another tool to refine extraction of the cavity based on adjacency data and then possibly place the implant based on the sensed data.

The power system of a preferred embodiment is a component of the system. The power system functions to give power to the implant electrical components (e.g. the plurality of electrodes 132 and pressure sensors). The power system may additionally, or alternatively, give power to the sensor processing control system 140 and any other electrical components. Additionally, the power system may give power to any other component requiring power. The power system may comprise of any general power source, or a multitude of power sources (e.g. electrical outlet, internal generator), but preferably comprises of a battery (or several batteries), more preferably rechargeable batteries. The power system may alternatively, be powered through wireless power coupling or other suitable forms of remote power delivery (e.g. induction). The power system may be implanted, as part of the implant body 110 or as a distinct system entity. As part of the implant body no, the power system may be located in a housing within the implant body, or may have a distinct housing connected to the implant body 110 for example the arm attachment 120. As a distinct system entity, the power system may be located outside of the body; or may include a combination of implantable and non-implantable components (e.g. internal inductably chargeable battery and an external charging device). The power system may be connected to each electrode through wiring, or may alternatively charge electrodes through induction or other means. In some variations, the power system may comprise of an external electrical source. External wiring may then be used to connect the power source to the implant body no. Alternatively, the power system may have a transmitter placed on, or near, the patient's body that can induce power into the implant body no and electrodes.

3. Method

As shown in FIG. 8, a method for positioning and orienting an orthopedic implant of a preferred embodiment includes, providing an implant body with a sensor system for surgical placement in a defined body cavity S110, collecting sensor data from the sensor system and converting the sensor data to tissue adjacency data S120, and reporting the tissue adjacency data through a feedback interface S130. The method may function to determine and/or place the implant in the appropriate place, in the body of a patient, as desired. The method is preferably implemented with a system as described above, but may be implemented with any suitable alternative system. As described above, the method may be implemented with both: an implant trial, wherein the method is applied to determine the correct size, shape, orientation, and position of the implant prior to using a "permanent" implant; and to the "permanent" implant, wherein the method is applied to place the implant of appropriate implant of the right size and shape at the desired position and orientation.

Block S110, which includes providing an implant body with a sensor system for surgical placement in a defined body cavity, functions to utilize a sensor-enhanced implant such as one described above. The implant body preferably includes a sensor system with sensors distributed on the surface of the implant. The implant is preferably one substantially like one of the system described herein.

In connection with providing an implant body, a human or robotic system may perform surgically placing the orthopedic implant in a desired position in the body of a patient. In particular, placing an implant will include placing the implant with a specific orientation wherein position and orientation feedback can be collected and used during the placement process. An implant arm may be used in assisting with the placement of the implant. In variations for an implant trial, placing the implant may further include determining the correct size and shape of the implant. Determining the correct size and shape of the implant may include multiple iterations of placing the implant trial using implant trials of distinct sizes and shapes until the correct size shape implant is found. For an actual functioning medical implant, placing an implant is preferably performed once, although it may be performed multiple times. Placing the medical implant may include superficially embedding/lodging the implant in adjacent tissue. In some variation, the implant may have "teeth" or some other type of protruding geometry to aid in embedding the implant within adjacent tissue.

During placement of the implant, the implant may be repositioned triggering updates to S120 and S130. Alternatively, S120, and S130 may be continuously or repeatedly performed. In addition to repositioning the implant, a user/medical professional may also change the implant body to a different type, size, and/or shape. An implant trial variation may be used in sizing and appropriately selecting a medical implant for implantation.

Block S120, which includes collecting sensor data from the sensor system and converting the sensor data to tissue adjacency data, functions to collect data through the implant body as to its position relative to the body and/or conditions surrounding the implant. Block S120 may include determining the implant adjacencies S122 and determining the implant orientation S124. Block S120 may be performed during or after placing the implant S110, during or after repositioning the implant, or at any other desired time. In some variations, Block S120 is performed after surgery to determine if the implant has moved or is still in the appropriate place.

Block S122, determining implant adjacencies is preferably a component of detecting the implant position S120. Determining implant adjacencies S122 functions in determining what tissue, if any, is adjacent to the implant. In a preferred variation, determining implant adjacencies S122 detects whether or not bone tissue is adjacent to the implant. In one preferred implementation, determining implant adjacencies S122 determines whether or not a spinal implant is positioned in-between and touching two vertebrae (above and below the implant).

Determining implant adjacencies S122 may include measuring the impedance of current through the tissue generated by electrodes on or near the adjacent surface of the implant. Measuring the impedance may help identify the type of tissue adjacent to the implant due to different levels of impedance in different types of tissue. Additionally and/or alternatively, determining implant adjacencies may include measuring the pressure along the surface of the implant. Measuring the external pressure along the surface of the implant may help determine if the implant surface is complete adjacent to a certain tissue type. Additionally, pressure along the surface may enable the determination how well the implant fits in the region. For example, an implant with a significantly different pressure along one surface may suggest that the implant is of an inappropriate size or shape.

Measuring impedance preferably includes setting electrical state of at least two electrodes, measuring an impedance metric between the two electrodes. Such impedance testing can be performed across multiple sets of electrodes. The multiple sets of electrodes can be selected to provide impedance information in different regions. Performing impedance testing can additionally include generating an impedance profile, which may use the multiple impedance values to determine a mapping of impedance in the vicinity of the implantable component. Measuring impedance can be used to provide a snapshot of current impedance conditions.

Measuring pressure preferably includes placing the implant such that the implant is lodged (i.e. relatively fixed) in place and removing any external pressures (e.g. from moving the implant around). In preferred variations for a spinal implant, to reduce gravitational effects, the patient is prone and the implant is placed downwards and lodged between two vertebrae such that pressure sensors on the implant are adjacent to the two vertebrae. Alternatively, gravity may be taken into account and the implant may be lodged in a seated position.

Measuring impedance and/or measuring pressure can further include processing a set of measurements and generating a tissue orientation map. The tissue orientation map functions to provide some relative position information concerning the implant and tissue or bone. In one variation, the tissue orientation map may be a one or two-dimensional measurement of alignment of bone tissue to one or more faces of the implant. For example, for a spinal fusion implant, measuring impedance may generate a measurement of position above a top surface of a first vertebrae and a measurement of position below a bottom surface of a second vertebrae (I.e. measuring the impedance on the surface of each endplate). In a second variation, the tissue orientation map may be a one or two-dimensional measurement of pressure along one or more surfaces of the implant. In a spinal fusion implant for this variation, the pressure mapping may comprise a mapping of the pressure along the top and bottom surface of the implant. The mapping may show uneven adjacencies between the implant and the adjacent vertebrae, due to the shape of the implant as compared to the vertebrae.

Determining implant adjacencies S122 may additionally determine how much of the implant side is adjacent to the tissue and the tissue density. For example, for a spinal implant, determining implant adjacency S120 may determine that only half the top of the implant is adjacent to a vertebra while the entire bottom is adjacent to the vertebra underneath it. Additionally in this example, determining implant adjacency S120 may determine the bone density of the vertebrae above and below the implant. In variations wherein multiple types of tissue are adjacent to a single side of the implant, determining adjacencies S122, may additionally determine the type of tissue and the amount of covering by that tissue for each side of the implant.

In a variation, where the sensor system of the implant includes a set of electrodes and a set of pressure sensors distributed on the surface of two faces of the implant, collecting sensor data from sensor system and converting the sensor data to tissue adjacency data can include: measuring impedance across multiple pairs of electrodes, sensing pressure at each of the pressure sensors, and converting the impedance to a map of tissue classifications and generating a sizing map of adjacent tissue based in part on pressure data collected from the pressure sensors and the map of tissue classifications.

Block S124, determining implant orientation, is preferably a component of detecting the implant position S120. Determining implant orientation S124 may function in measuring the orientation of the implant without direct visual contact. In preferred variations, determining implant orientation S124 is with respect to a detector outside of the patient, but may alternatively be with respect to the earth (e.g. through the use of a gyroscope). In determining implant orientation S124 may include sending an orientation signal from the implant to a receiver, wherein the receiver determines the orientation of the implant from the signal. Determining the implant orientation S124 may be implemented with the implant trial to determine the correct orientation of the actual implant prior to placing the implant S110 for the actual implant.

Determining implant orientation S124 can include determining the amplitude of the signal transferred between the implantable antenna and a non-implantable antenna. The signal received by a receiving antenna which will be attenuated by the angle and distance between the transmitting and receiving antenna assuming a fixed voltage/frequency in the transmitting antenna. In one variation, the non-implantable antenna is the receiving antenna and the implantable antenna is the transmitting antenna. In another variation, the non-implantable antenna is the transmitting antenna and the implantable antenna is the receiving antenna. In some variations, both antennas serve as receiving and transmitting in different instances/modes.

Angle and distance can be further parcellated and detected by adjusting the angle of the receiver antenna, moving the receiver antenna, and/or comparing the signal with other receiver antennas displaced by some distance and/or placed in a different angle. For a given antenna-to-antenna distance and planar transmitter and receiver antennas, the maximum received power will occur when two antennas are parallel and minimum when they are perpendicular. By collecting signals at different relative angles and determining the received power at each angle, the angle of the transmitter antenna can be determined. Active rotation (through actuated motion or through manual motion) may be used. For example, rotating the receiver antenna relative to the implant antenna can collect a set of signals measurements at distinct measurements. Additionally or alternatively, an array of antennas in the implantable and/or non-implantable components can provide angular detection.

Once the angle is known and the transmitter power output and antenna geometries fixed, the distance can be determined based on the power of the received signal for any given angle between the two antennas. A simple example of this approach is when the antennas are arranged such that they are parallel and the transmitter output is fixed, as is antenna geometry. In this example, the power of the signal received by the receiver antenna will only vary on the distance between the two antennas such that the signal power can be used to determine the distance between the receiver and transmitter antennas. This process can be done using both a single receiver antenna or an antenna array with antennas located in positions to easily allow the location and orientation of the implant to be determined using the above-mentioned method. The latter approach also means that an antenna may never need to be moved or attenuated in terms of angle (but may be either moved and/or attenuated).

In an alternative variation, determining implant orientation S124 can include receiving the information from an inertial measuring unit (IMU). The IMU preferably orients itself with respect to the gravity of the earth. The information is preferably obtained from the device wirelessly. Alternatively, the orientation information may be received from a gyroscope, or any other gravitationally orienting device.

In some variations determining implant orientation S124 may include determining implant orientation with respect to internal patient organs or systems, for example a specific vertebra or multiple vertebrae of the patient. In these variations, placing an implant S110 may further include placing (e.g. implanting, imprinting, or injecting) orientable components on the desired organ or system. Determining implant orientation S124 may then further detect the implant orientation with respect to the desired organ or system. In one preferred example, placing an implant S110 imprints an orientable component into the vertebrae directly above and below the spinal implant. Thus, determining implant orientation S124 may monitor the implant orientation with respect to both adjacent vertebrae.

Processing of implant adjacencies and/or implant orientation may additionally be used to determine various forms of conclusions related to implant position. Preferably, the implant adjacencies and/or implant orientation information can be synthesized into more readily used information for a user/surgeon. In one variation, determining implant orientation S124 can be coordinated with determining implant adjacencies S122 and used to form a tissue map of the surgical space, which may extend beyond immediate vicinity of the implants current position. This variation uses the historical implant adjacency data along with implant orientation to map a volume of space. This is preferably performed while the implant is being repositioned and moved by a user/surgeon assessing the proper sizing and positioning. Impedance measurements can be collected as the implant body is being reoriented, and from this a three dimensional map of impedance can be generated.

Block S130, which includes reporting implant position, functions to provide feedback. Implant adjacencies and/or orientation can be reported in a variety of mediums including graphical visualizations, (e.g., 2D or 3D maps), visual indicators (e.g., indicator lights), informational reports or displays (e.g., measurement readings), audio (e.g., sounds indicating alignment), tactile (e.g., vibrational indication of alignment), and/or any suitable form of feedback. In one preferred variation, reporting implant position data S130 is performed through a human-computer user interface, which may include a display and audio system, but any suitable feedback device may be used such as an augmented reality display and/or virtual reality system. In one implementation of this variation, reporting implant position data S130 provides 2D and/or 3D mappings of adjacent tissue data through a user interface. In another preferred variation, reporting implant position data S130 can be carried out through a user feedback system integrated into an arm attachment or another element of system.

In one variation, the implant adjacency and implant orientation can be used in combination with external body imaging sources. In this variation, the method may further include collecting body image data from an external imaging source, detecting body position relative to implant device, and reconciling implant position to the body image data.

Through this variation, the implant can be rendered in combination with other forms of body imaging such as a CT scan Reporting of implant position is preferably used in assisting a human user. The method may additionally or alternatively be used in controlling external systems such as other medical equipment. In a variation where the implant surgery is performed or assisted by a robotic surgery device, then the reported implant position may be used to assist in control of the robotic surgery device. In such a variation, reporting the tissue adjacency data through a feedback interface comprises communicating the tissue adjacency data (e.g., a sizing map of adjacent tissue) to a robot surgery tool; and then additionally controlling the robot surgery tool in part based on the sizing map of adjacent tissue. Controlling the robot surgery tool can include informing path for extracting tissue, inserting an implant, orienting an implant, and/or controlling any suitable aspect of the robotic system.

When a user has the implant in a desired position, the status of the implant position can be recorded and set as a target position for the subsequent portion of the surgery. It could additionally be recorded and used as a reference measurement for post-surgery evaluation of implant migration.

The systems and methods of the embodiments can be embodied and/or implemented at least in part as a machine configured to receive a computer-readable medium storing computer-readable instructions. The instructions can be executed by computer-executable components integrated with the application, applet, host, server, network, website, communication service, communication interface, hardware/firmware/software elements of a user computer or mobile device, wristband, smartphone, or any suitable combination thereof. Other systems and methods of the embodiment can be embodied and/or implemented at least in part as a machine configured to receive a computer-readable medium storing computer-readable instructions. The instructions can be executed by computer-executable components integrated with apparatuses and networks of the type described above. The computer-readable medium can be stored on any suitable computer readable media such as RAMs, ROMs, flash memory, EEPROMs, optical devices (CD or DVD), hard drives, floppy drives, or any suitable device. The computer-executable component can be a processor but any suitable dedicated hardware device can (alternatively or additionally) execute the instructions.

As a person skilled in the art will recognize from the previous detailed description and from the figures and claims, modifications and changes can be made to the embodiments of the invention without departing from the scope of this invention as defined in the following claims.

We claim:

1. A system for orthopedic implant surgery comprising:
   an implant body made of a solid rigid structure, wherein the implant body is an implant trial body;
   an arm attachment that extends from and physically couples to the implant body;
   a sensor system integrated into the implant body, the sensor system comprising of at least a plurality of electrodes positioned within the implant body such there is at least one exposed region on the surface of the implant body for each electrode of the plurality of electrodes;
   a sensor processing control system communicatively coupled to the sensor system, wherein at least a portion of the sensor processing control system is housed in the arm attachment, the sensor processing control system configured with instructions that when executed cause the sensor processing control system to collect sensor data from the sensor system and generate adjacency data from the sensor data; and
   an implant feedback system that updates state based in part on the adjacency data.

2. The system of claim 1, wherein the arm attachment removably couples to the implant body.

3. The system of claim 1, further comprising an orienting system configured to report the orientation of the implant body corresponding to the adjacency data.

4. The system of claim 1, wherein the implant body is a spinal implant for implantation in a patient.

5. The system of claim 1, further comprising an oriented antenna integrated with the implant body; and an external antenna array comprising antennas with multiple orientations; wherein in a orienting function mode, the strength coupling between the oriented antenna and the antenna array determines the relative orientation of the implantable orienting component with respect to the non-implantable orienting component.

6. The system of claim 1, further comprising an oriented antenna integrated with the implant body; and an external antenna array comprising antennas with multiple orientations; wherein in a positioning mode, the strength coupling between the oriented antenna and the antenna array determines a position of the oriented antenna.

7. A system comprising:
   an implant body made of a solid rigid structure, wherein the implant body is an implant trial body;
   an arm attachment that extends from and physically couples to the implant body;
   a sensor system integrated into the implant body, the sensor system comprising of at least a plurality of electrodes positioned within the implant body such there is at least one exposed region on the surface of the implant body for each electrode of the plurality of electrodes;
   a sensor processing control system communicatively coupled to the sensor system, the sensor processing control system configured with instructions that when executed cause the sensor processing control system to collect sensor data from the sensor system and generate adjacency data from the sensor data, wherein the adjacency data is a sizing map; and
   an implant feedback system that updates state based in part on the adjacency data, wherein the feedback system comprises a graphical user interface that is configured to display the sizing map.

8. The system of claim 7, wherein at least a portion of the sensor processing control system is housed in the arm attachment.

9. A system comprising:
   an implant body made of a solid rigid structure, wherein the implant body is an implant trial body;
   an arm attachment that extends from and physically couples to the implant body;
   a sensor system integrated into the implant body, the sensor system comprising of at least a plurality of electrodes positioned within the implant body such there is at least one exposed region on the surface of the implant body for each electrode of the plurality of electrodes;
   a sensor processing control system communicatively coupled to the sensor system, the sensor processing control system configured with instructions that when executed cause the sensor processing control system to collect sensor data from the sensor system and generate adjacency data from the sensor data;
an implant feedback system that updates state based in part on the adjacency data; and
a robotic surgery system that communicatively couples to the feedback interface, and wherein the robotic surgery system is at least partially controlled based on the adjacency data.

10. A system comprising:
an implant body made of a solid rigid structure, wherein the implant body is an implant trial body;
an arm attachment that extends from and physically couples to the implant body;
a sensor system integrated into the implant body, the sensor system comprising of at least a plurality of electrodes positioned within the implant body such there is at least one exposed region on the surface of the implant body for each electrode of the plurality of electrodes;
a sensor processing control system communicatively coupled to the sensor system, the sensor processing control system comprising an electrode control system configured to measure impedance across multiple pairs of electrodes from the plurality of electrodes, the sensor processing control system configured with instructions that when executed cause the sensor processing control system to collect sensor data from the sensor system and generate adjacency data from the sensor data and generate a map of tissue classifications from the measured impedance; and
an implant feedback system that updates state based in part on the adjacency data.

11. The system of claim 10, wherein the plurality of electrodes comprises a subset of electrodes positioned on a first external face of the implant body and a second subset of electrodes positioned on a second external face of the implant body; wherein the first and second external faces are on opposite sides of the implant body; and wherein the map of tissue classifications are mapped for the first and second external faces.

12. The system of claim 10, wherein the sensor system further comprises a plurality of pressure sensors; and wherein the instructions to generate adjacency data from the sensor data generate a sizing map of adjacent tissue based in part on pressure data collected from the pressure sensors and the map of tissue classifications.

13. A system comprising:
an implant body made of a solid rigid structure, wherein the implant body is an implant trial body;
an arm attachment that extends from and physically couples to the implant body;
a sensor system integrated into the implant body, the sensor system comprising of at least a plurality of electrodes positioned within the implant body such there is at least one exposed region on the surface of the implant body for each electrode of the plurality of electrodes, the sensor system comprising a plurality of pressure sensors;
a sensor processing control system communicatively coupled to the sensor system, the sensor processing control system configured with instructions that when executed cause the sensor processing control system to collect sensor data from the sensor system and generate adjacency data from the sensor data and generate a sizing map based in part on pressure data collected from the pressure sensors; and
an implant feedback system that updates state based in part on the adjacency data.

14. The system of claim 13, wherein the plurality of pressure sensors comprise a subset of pressure sensors are positioned on a first external face of the implant body and a second subset of electrodes are positioned on a second external face of the implant body; wherein the first and second external faces are on opposite sides of the implant body; and wherein the sizing map includes sizing data mapped for the first and second external faces.

15. A system comprising:
an implant body made of a solid rigid structure, wherein the implant body is an implant trial body;
an arm attachment that extends from and physically couples to the implant body;
a sensor system integrated into the implant body, the sensor system comprising of at least a plurality of electrodes positioned within the implant body such there is at least one exposed region on the surface of the implant body for each electrode of the plurality of electrodes;
a sensor processing control system communicatively coupled to the sensor system, the sensor processing control system configured with instructions that when executed cause the sensor processing control system to collect sensor data from the sensor system and generate adjacency data from the sensor data;
an orienting system configured to report the orientation of the implant body corresponding to the adjacency data; and
a second implant body that is an orthopedic implant for implantation in a patient, wherein the second implant body comprises a second orienting system configured to report the orientation of the second implant body; and
an implant feedback system that updates state based in part on the adjacency data, wherein the feedback system reports a comparison of the orientation of the second implant body to the orientation corresponding to the adjacency data.

16. A system comprising:
an implant body made of a solid rigid structure, wherein the implant body is an implant trial body;
an arm attachment that extends from and physically couples to the implant body;
a sensor system integrated into the implant body, the sensor system comprising of at least a plurality of electrodes positioned within the implant body such there is at least one exposed region on the surface of the implant body for each electrode of the plurality of electrodes;
a sensor processing control system communicatively coupled to the sensor system, the sensor processing control system configured with instructions that when executed cause the sensor processing control system to collect sensor data from the sensor system and generate adjacency data from the sensor data;
an orienting system configured to report the orientation of the implant body corresponding to the adjacency data;
a second implant body that is an orthopedic implant for implantation in a patient, wherein the second implant body comprises a second sensor system and a second sensor processing control system communicatively coupled to the sensor system, the second processing system configured with instructions that when executed cause the second sensor processing control system to collect a second set of sensor data from the second sensor system and generate adjacency data of the second implant body from the sensor data; and an implant feedback system that updates state based in part on the adjacency data, wherein the implant feedback system is configured to present a comparison of the adjacency data from the implant trial body and the adjacency data of the second implant body during use of the second implant body.

17. A method for checking implantation of an orthopedic implant comprising:

providing an implant body for surgical placement in a defined body cavity, wherein the implant comprises of a sensor system with sensors distributed on the surface of the implant, wherein the sensor system comprises a set of electrodes and a set of pressure sensors distributed on the surface of two faces of the implant;

collecting sensor data from the sensor system, which comprises measuring impedance across multiple pairs of electrodes and sensing pressure at each of the pressure sensors;

converting the sensor data to tissue adjacency data, which comprises converting the impedance to a map of tissue classifications and generating a sizing map of adjacent tissue based in part on pressure data collected from the pressure sensors and the map of tissue classifications; and reporting the tissue adjacency data through a feedback interface and displaying a graphical representation of the sizing map of adjacent tissue.

18. A method for checking implantation of an orthopedic implant comprising:

providing an implant body for surgical placement in a defined body cavity, wherein the implant comprises of a sensor system with sensors distributed on the surface of the implant;

collecting sensor data from the sensor system;

converting the sensor data to tissue adjacency data and generating a sizing map of adjacent tissue;

reporting the tissue adjacency data through a feedback interface, which comprises communicating the sizing map of adjacent tissue to a robot surgery tool; and controlling the robot surgery tool in part based on the sizing map of adjacent tissue.

19. The method of claim 18, and wherein reporting the tissue adjacency data comprises displaying a graphical representation of the sizing map of adjacent tissue.

* * * * *